(12) United States Patent
Varsani et al.

(10) Patent No.: US 8,163,557 B2
(45) Date of Patent: Apr. 24, 2012

US008163557B2

(54) CHIMAERIC HUMAN PAPILLOMAVIRUS 16 L1 VIRUS-LIKE PARTICLES AND A METHOD FOR PREPARING THE PARTICLES

(75) Inventors: Arvind Devshi Varsani, Cape Town (ZA); Edward Peter Rybicki, Cape Town (ZA)

(73) Assignee: University of Cape Town, Cape Town (ZA)

( * ) Notice: Subject to any disclaimer, the term of this patent is extended or adjusted under 35 U.S.C. 154(b) by 195 days.

(21) Appl. No.: 12/174,104

(22) Filed: Jul. 16, 2008

(65) Prior Publication Data
US 2009/0047302 A1   Feb. 19, 2009

Related U.S. Application Data

(60) Division of application No. 10/514,878, filed on Mar. 18, 2005, now Pat. No. 7,407,807, which is a continuation of application No. PCT/IB03/01912, filed on May 19, 2003.

(30) Foreign Application Priority Data

May 17, 2002   (ZA) ...................................... 02/3957

(51) Int. Cl.
*A61K 39/12* (2006.01)
*A61K 38/00* (2006.01)

(52) U.S. Cl. .................... 435/456; 435/91.4; 435/91.33; 435/483; 435/484; 435/477; 424/186.1; 424/199.1; 424/196.11

(58) Field of Classification Search .................. None
See application file for complete search history.

(56) References Cited

OTHER PUBLICATIONS

Slupetzky et al. (20010 Chimeric papillomavirus-like particles expressing a foreign epitope on capsid surface loops, J. Gen. Virol., vol. 82, Pt 11, 2799-2804.*
Chen et al. (2000) Structure of small virus-like particles assembled from the L1 protein of human papillomavirus 16, Mol. Cell, vol. 5, No. 3, pp. 557-567.*
Varsani et al. (2003) Chimeric Human Papillomavirus Type 16 (HPV-16) L1 Particles Presenting the Common Neutralizing Epitope for the L2 Minor Capsid Protein of HPV-6 and HPV-16, J. Virol., vol. 77, No. 15, pp. 8386-8393.*
Kimbauer et al. (1993) Efficient self-assembly of human papillomavirus type 16 L1 and L1-L2 into virus-like particles, J. Virol., vol. 67, No. 12, pp. 6929-6936.*
Kawana et al. (2001) Nasal immunization of mice with peptide having a cross-neutralization epitope on minor capsid protein L2 of human papillomavirus type 16 elicit systemic and mucosal antibodies, Vaccine, vol. 19, issue 11-12, pp. 1496-1502.*

* cited by examiner

*Primary Examiner* — Anand Desai
*Assistant Examiner* — Samuel Liu
(74) *Attorney, Agent, or Firm* — Norris McLaughlin & Marcus PA

(57) ABSTRACT

A method for producing a chimaeric human papillomavirus (HPV) L1 polypeptide containing a heterologous peptide, and in particular, a HPV L2 peptide comprising the steps of introducing a DNA sequence coding for the heterologous peptide into a DNA sequence coding for the L1 polypeptide; introducing the DNA sequence including the sequences for the L1 polypeptide and heterologous peptide into a host cell in which the DNA sequence can be expressed; causing expression of the DNA sequence; and recovering the resulting chimaeric L1 polypeptide which includes the heterologous peptide. The invention also describes a vector for use in the method, a host cell containing the vector, and a vaccine including the chimaeric HPV L1 polypeptide produced according to the method.

10 Claims, 16 Drawing Sheets

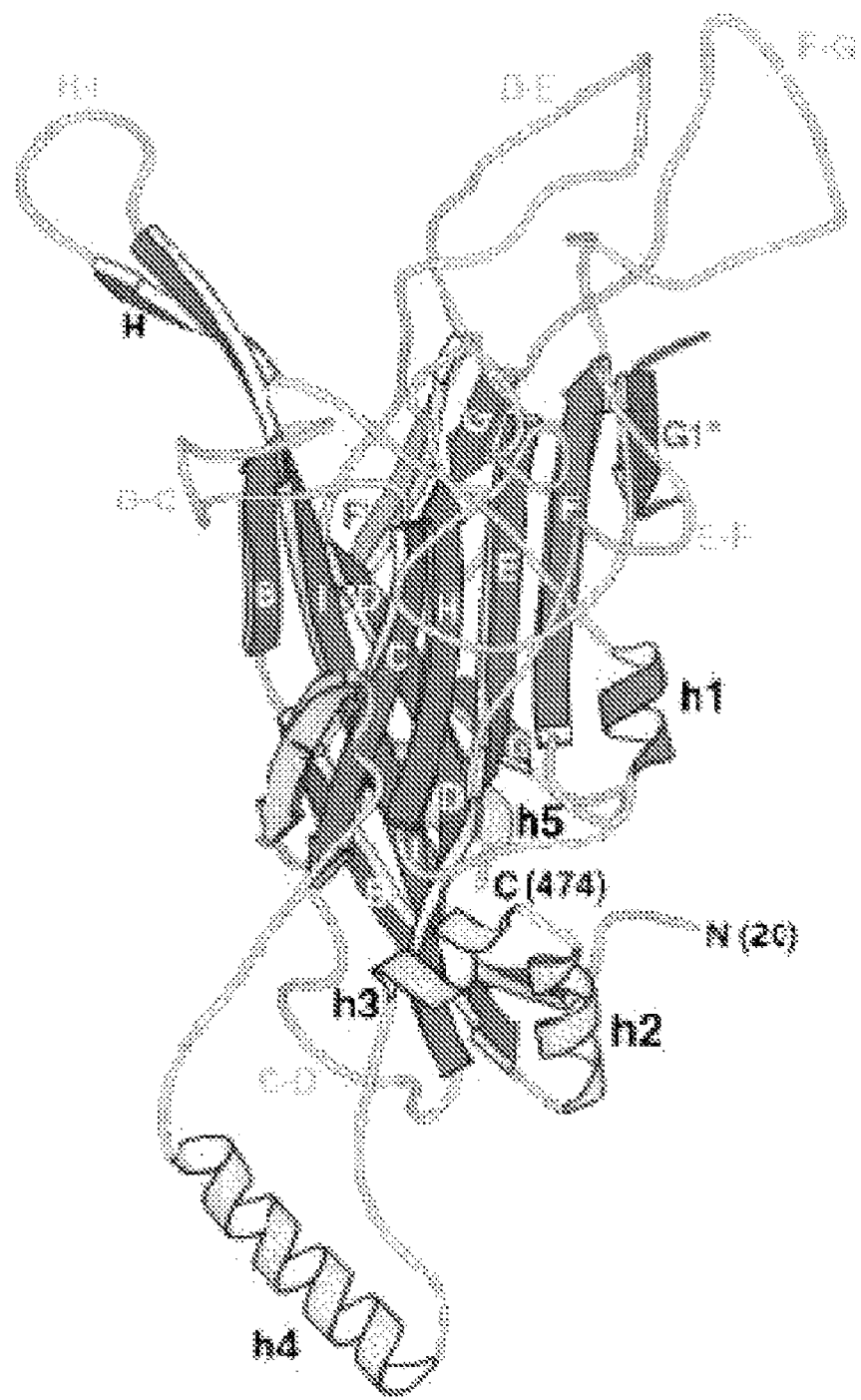
Figure 2 – Prior Art

```
SEQ  Sa-11: 1518 bp;
Composition   486  A;  293  C;  287  G;  452  T;  0 OTHER
Percentage:   32%  A;  19%  C;  19%  G;  30%  T;  0%OTHER Molecular Weight (kDa):  ssDNA: 468.63     dsDNA: 935.7
ORIGIN
1        ATGTCTCTTT  GGCTGCCTAG  TGAGGCCACT  GTCTACTTGC  CTCCTGTCCC  AGTATCTAAG
61       GTTGTAAGCA  CGGATGAATA  TGTTGCACGC  ACAAACATAT  ATTATCATGC  AGGGACATCC
121      AGACTACTTG  CAGTTGGACA  TCCCTATTTT  CCTATTAAAA  AACCTAACAA  TAACAAAATA
181      TTAGTTCCTA  AAGTATCAGG  ATTACAATAC  AGGGTATTTA  GAATACATTT  ACCTGACCCC
241      AATAAGTTTG  GTTTTCCTGA  CACCTCATTT  TATAATCCAG  ATACACAGCG  GCTGGTTTGG
301      GCCTGTGTAG  GTGTTGAGGT  AGGCCGTGGT  CAGCCATTAG  GTGTGGGCAT  TAGTGGCCAT
361      CCTTTATTAA  ATAAATTGGA  TGACACAGAA  AATGCTAGTG  CTTATGCAGC  AAATGCAGGT
421      GTGGATAATA  GAGAATGTAT  ATCTATGGAT  TACAAACAAA  CACAATTGTG  TTTAATTGGT
481      TGCAAACCAC  CTATAGGGGA  CACTGGGGC   AAAGGATCCC  CATGTACCAA  TGTTGCAGTA
541      AATCCAGGTG  ATTGTCCACC  ATTAGAGTTA  ATAAACACAG  TTATTCAGGA  TGGTGATATG
601      GTTGATACTG  GCTTTGGTGC  TATGGACTTT  ACTACATTAC  AGGCTAACAA  AAGTGAAGTT
661      CCACTGGATA  TTTGTACATC  TATTTGCAAA  TATCCAGATT  ATATTAAAAT  GGTGTCAGAA
721      CCATATGGCG  ACAGCTTATT  TTTTTATTTA  CGGAGGGAAC  AAATGTTTGT  TAGACATTTA
781      TTTAATAGGG  CTGGTACTGT  TGGTGAAAAT  GTACCAGACG  ATTTATACAT  TAAAGGCTCT
841      GGGTCTACTG  CAAATTTAGC  CAGTTCAAAT  TATTTTCCTA  CACCTAGTGG  TTCTATGGTT
901      ACCTCTGATG  CCCAAATATT  CAATAAACCT  TATTGGTTAC  AACGAGCACA  GGGCCACAAT
961      AATGGCATTT  GTTGGGGTAA  CCAACTATTT  GTTACTGTTG  TTGATACTAC  ACGCAGTACA
1021     AATATGTCAT  TATGTGCTGC  CATATCTACT  TCAGAAACTA  CATATAAAAA  TACTAACTTT
1081     AAGGAGTACC  TACGACATGG  GGAGGAATAT  GATTTACAGT  TTATTTTTCA  ACTGTGCAAA
1141     ATAACCTTAA  CTGCAGACGT  TATGACATAC  ATACATTCTA  TGAATTCCAC  TATTTTGGAG
1201     GACTGGAATT  TTGGTCTACA  ACCTCCCCCA  GGAGGCACAC  TAGAAGATAC  TTATAGGTTT
1261     GTAACATCCC  AGGCAATTGC  TTGTCAAAAA  CATACACCTC  CAGCACCTAA  AGAAGATCCC
1321     CTTAAAAAAT  ACACTTTTTG  GGAAGTAAAT  TTAAAGGAAA  AGTTTTCTGC  AGACCTAGAT
1381     CAGTTTCCTT  TAGGACGCAA  ATTTTTACTA  CAAGCAGGAT  TGAAGGCCAA  ACCAAAATTT
1441     ACATTAGGAA  AACGAAAAGC  TACACCCACC  ACCTCATCTA  CCTCTACAAC  TGCTAAACGC
1501     AAAAAACGTA  AGCTGTAA
```

Figure 3 (SEQ ID NO: 2)

```
Translation of Sa-11(1-1518)
Universal code
Total amino acid number: 505, MW=56196
Max ORF: 1-1515, 505 AA, MW=56196

ORIGIN
1          MSLWLPSEAT  VYLPPVPVSK  VVSTDEYVAR  TNIYYHAGTS  RLLAVGHPYF  PIKKPNNNKI
61         LVPKVSGLQY  RVFRIHLPDP  NKFGFPDTSF  YNPDTQRLVW  ACVGVEVGRG  QPLGVGISGH
121        PLLNKLDDTE  NASAYAANAG  VDNRECISMD  YKQTQLCLIG  CKPPIGEHWG  KGSPCTNVAV
181        NPGDCPPLEL  INTVIQDGDM  VDTGFGAMDF  TTLQANKSEV  PLDICTSICK  YPDYIKMVSE
241        PYGDSLFFYL  RREQMFVRHL  FNRAGAVGEN  VPDDLYIKGS  GSTANLASSN  YFPTPSGSMV
301        TSDAQIFNKP  YWLQRAQGHN  NGICWGNQLF  VTVVDTTRST  NMSLCAAIST  SETTYKNTNF
361        KEYLRHGEEY  DLQFIFQLCK  ITLTADVMTY  IHSMNSTILE  DWNFGLQPPP  GGTLEDTYRF
421        VTSQAIACQK  HTPPAPKEDP  LKKYTFWEVN  LKEKFSADLD  QFPLGRKFLL  QAGLKAKPKF
481        TLGKRKATPT  TSSTSTTAKR  KKRKL*
```

Figure 4 (SEQ ID NO: 3)

```
SEQ  Sa-Aopt: 1518 bp;
Composition   486  A;  289  C;  289  G;  454  T;  0 OTHER
Percentage:   32%  A;  19%  C;  19%  G;  30%  T;  0%OTHER Molecular Weight (kDa):  ssDNA: 468.74    dsDNA: 935.7
ORIGIN
1       ATGTCTCTTT  GGCTGCCTAG  TGAGGCCACT  GTCTACTTGC  CTCCTGTCCC  AGTATCTAAG
61      GTTGTAAGCA  CGGATGAATA  TGTTGCACGC  ACAAACATAT  ATTATCATGC  AGGGACATCC
121     AGACTACTTG  CAGTTGGACA  TCCCTATTTT  CCTATTAAAA  AACCTAACAA  TAACAAAATA
181     TTAGTTCCTA  AAGTATCAGG  ATTACAATAC  AGGGTATTTA  GAATACATTT  ACCTGACCCC
241     AATAAGTTTG  GTTTTCCTGA  CACCTCATTT  TATAATCCAG  ATACACAGCG  GCTGGTTTGG
301     GCCTGTGTAG  GTGTTGAGGT  AGGCCGTGGT  CAGCCATTAG  GTGTGGGCAT  TAGTGGCCAT
361     CCTTTATTAA  ATAAATTGGA  TGACACAGAA  AATGCTAGTG  CTTATGCAGC  AAATGCAGGT
421     GTGGATAATA  GAGAATGTAT  ATCTATGGAT  TACAAACAAA  CACAATTGTG  TTTAATTGGT
481     TGCAAACCAC  CTATAGGGGA  ACACTGGGGC  AAAGGATCCT  TAGTGGAAGA  AACTAGTTTT
541     ATTGATGCTG  GTGCACCACC  ATTAGAGTTA  ATAAACACAG  TTATTCAGGA  TGGTGATATG
601     GTTGATACTG  GCTTTGGTGC  TATGGACTTT  ACTACATTAC  AGGCTAACAA  AAGTGAAGTT
661     CCACTGGATA  TTTGTACATC  TATTTGCAAA  TATCCAGATT  ATATTAAAAT  GGTGTCAGAA
721     CCATATGGCG  ACAGCTTATT  TTTTTATTTA  CGGAGGGAAC  AAATGTTTGT  TAGACATTTA
781     TTTAATAGGG  CTGGTACTGT  TGGTGAAAAT  GTACCAGACG  ATTTATACAT  TAAAGGCTCT
841     GGGTCTCTG   CAAATTTAGC  CAGTTCAAAT  TATTTTCCTA  CACCTAGTGG  TTCTATGGTT
901     ACCTCTGATG  CCCAAATATT  CAATAAACCT  TATTGGTTAC  AACGAGCACA  GGGCCACAAT
961     AATGGCATTT  GTTGGGGTAA  CCAACTATTT  GTTACTGTTG  TTGATACTAC  ACGCAGTACA
1021    AATATGTCAT  TATGTGCTGC  CATATCTACT  TCAGAAACTA  CATATAAAAA  TACTAACTTT
1081    AAGGAGTACC  TACGACATGG  GGAGGAATAT  GATTTACAGT  TTATTTTTCA  ACTGTGCAAA
1141    ATAACCTTAA  CTGCAGACGT  TATGACATAC  ATACATTCTA  TGAATTCCAC  TATTTTGGAG
1201    GACTGGAATT  TTGGTCTACA  ACCTCCCCCA  GGAGGCACAC  TAGAAGATAC  TTATAGGTTT
1261    GTAACATCCC  AGGCAATTGC  TTGTCAAAAA  CATACACCTC  CAGCACCTAA  AGAAGATCCC
1321    CTTAAAAAAT  ACACTTTTTG  GGAAGTAAAT  TTAAAGGAAA  AGTTTTCTGC  AGACCTAGAT
1381    CAGTTTCCTT  TAGGACGCAA  ATTTTTACTA  CAAGCAGGAT  TGAAGGCCAA  ACCAAAATTT
1441    ACATTAGGAA  AACGAAAAGC  TACACCCACC  ACCTCATCTA  CCTCTACAAC  TGCTAAACGC
1501    AAAAAACGTA  AGCTGTAA
```

Figure 5 (SEQ ID NO: 4)

```
Translation of ChiA(1-1518)
Universal code
Total amino acid number: 505, MW=56288
Max ORF: 1-1515, 505 AA, MW=56288

ORIGIN
1       MSLWLPSEAT  VYLPPVPVSK  VVSTDEYVAR  TNIYYHAGTS  RLLAVGHPYF  PIKKPNNNKI
61      LVPKVSGLQY  RVFRIHLPDP  NKFGFPDTSF  YNPDTQRLVW  ACVGVEVGRG  QPLGVGISGH
121     PLLNKLDDTE  NASAYAANAG  VDNRECISMD  YKQTQLCLIG  CKPPIGEHWG  KGSLVEETSF
181     IDAGAPPLEL  INTVIQDGDM  VDTGFGAMDF  TTLQANKSEV  PLDICTSICK  YPDYIKMVSE
241     PYGDSLFFYL  RREQMFVRHL  FNRAGTVGEN  VPDDLYIKGS  GSTANLASSN  YFPTPSGSMV
301     TSDAQIFNKP  YWLQRAQGHN  NGICWGNQLF  VTVVDTTRST  NMSLCAAIST  SETTYKNTNF
361     KEYLRHGEEY  DLQFIFQLCK  ITLTADVMTY  IHSMNSTILE  DWNFGLQPPP  GGTLEDTYRF
421     VTSQAIACQK  HTPPAPKEDP  LKKYTFWEVN  LKEKFSADLD  QFPLGRKFLL  QAGLKAKPKF
481     TLGKRKATPT  TSSTSTTAKR  KKRKL*
```

Figure 6 (SEQ ID NO: 5)

```
SEQ  Sa-Copt: 1518 bp;
Composition   485   A;  293   C;  286   G;  454   T;  0 OTHER
Percentage:   32%   A;  19%   C;  19%   G;  30%   T;  0%OTHER Molecular Weight (kDa): ssDNA: 468.59    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGT CAGCCATTAG GTGTGGGCAT TAGTGGCCAT
361     CCTTTATTAA ATAAATTGGA TGACACAGAA TTAGTGGAAG AAACTAGTTT TATTGATGCT
421     GGTGCACCAA GAGAATGTAT ATCTATGGAT TACAAACAAA CACAATTGTG TTTAATTGGT
481     TGCAAACCAC CTATAGGGGA ACACTGGGGC AAAGGATCCC CATGTACCAA TGTTGCAGTA
541     AATCCAGGTG ATTGTCCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGG CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAGGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAC TAGAAGATAC TTATAGGTTT
1261    GTAACATCCC AGGCAATTGC TTGTCAAAAA CATACACCTC CAGCACCTAA AGAAGATCCC
1321    CTTAAAAAAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCAAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 7 (SEQ ID NO: 6)

```
Translation of ChiC(1-1518)
Universal code
Total amino acid number: 505, MW=56337
Max ORF: 1-1515, 505 AA, MW=56337

ORIGIN
1         MSLWLPSEAT VYLPPVPVSK VVSTDEYVAR TNIYYHAGTS RLLAVGHPYF PIKKPNNNKI
61        LVPKVSGLQY RVFRIHLPDP NKFGFPDTSF YNPDTQRLVW ACVGVEVGRG QPLGVGISGH
121       PLLNKLDDTE LVEETSFIDA GAPRECISMD YKQTQLCLIG CKPPIGEHWG KGSPCTNVAV
181       NPGDCPPLEL INTVIQDGDM VDTGFGAMDF TTLQANKSEV PLDICTSICK YPDYIKMVSE
241       PYGDSLFFYL RREQMFVRHL FNRAGTVGEN VPDDLYIKGS GSTANLASSN YFPTPSGSMV
301       TSDAQIFNKP YWLQRAQGHN NGICWGNQLF VTVVDTTRST NMSLCAAIST SETTYKNTNF
361       KEYLRHGEEY DLQFIFQLCK ITLTADVMTY IHSMNSTILE DWNFGLQPPP GGTLEDTYRF
421       VTSQAIACQK HTPPAPKEDP LKKYTFWEVN LKEKFSADLD QFPLGRKFLL QAGLKAKPKF
481       TLGKRKATPT TSSSTTAKR KKRKL*
```

Figure 8 (SEQ ID NO: 7)

```
SEQ  Sa-eopt: 1518 bp;
Composition   480  A;  285  C;  294  G;  459  T;  0 OTHER
Percentage:    32% A;  19% C;  19% G;  30% T;  0%OTHER Molecular Weight (kDa): ssDNA: 468.87    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGT CAGCCATTAG GTGTGGGCAT TAGTGGCCAT
361     CCTTTTATTAA ATAAATTGGA TGACACAGAA AATGCTAGTG CTTATGCAGC AAATGCAGGT
421     GTGGATAATA GAGAATGTAT ATCTATGGAT TACAAACAAA CACAATTGTG TTTAATTGGT
481     TGCAAACCAC CTATAGGGGA ACACTGGGGC AAAGGATCCC CATGTACCAA TGTTGCAGTA
541     AATCCAGGTG ATTGTCCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGG CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAGGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAC TAGAAGATAC TTATAGGTTT
1261    GTAACATCCC AGGCAATTGC TTGTCAAAAA TTAGTGGAAG AAACTAGTTT TATTGATGCT
1321    GGTGCACCAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCCAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 9 (SEQ ID NO: 8)

```
Translation of ChiE(1-1518)
Universal code
Total amino acid number: 505, MW=56117
Max ORF: 1-1515, 505 AA, MW=56117

ORIGIN
1       MSLWLPSEAT VYLPPVPVSK VVSTDEYVAR TNIYYHAGTS RLLAVGHPYF PIKKPNNNKI
61      LVPKVSGLQY RVFRIHLPDP NKFGFPDTSF YNPDTQRLVW ACVGVEVGRG QPLGVGISGH
121     PLLNKLDDTE NASAYAANAG VDNRECISMD YKQTQLCLIG CKPPIGEHWG KGSPCTNVAV
181     NPGDCPPLEL INTVIQDGDM VDTGFGAMDF TTLQANKSEV PLDICTSICK YPDYIKMVSE
241     PYGDSLFFYL RREQMFVRHL FNRAGTVGEN VPDDLYIKGS GSTANLASSN YFPTPSGSMV
301     TSDAQIFNKP YWLQRAQGHN NGICWGNQLF VTVVDTTRST NMSLCAAIST SETTYKNTNF
361     KEYLRHGEEY DLQFIFQLCK ITLTADVMTY IHSMNSTILE DWNFGLQPPP GGTLEDTYRF
421     VTSQAIACQK LVEETSFIDA GAPYTFWEVN LKEKFSADLD QFPLGRKFLL QAGLKAKPKF
481     TLGKRKATPT TSSTSTTAKR KKRKL*
```

Figure 10 (SEQ ID NO: 9)

```
SEQ  Sa-Fopt: 1518 bp;
Composition   484  A;  291  C;  290  G;  453  T;  0 OTHER
Percentage:   32%  A;  19%  C;  19%  G;  30%  T;  0%OTHER Molecular Weight (kDa): ssDNA: 468.71    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGC CAGCCATTAG GTGTGGGCAT TAGTGGCCAT
361     CCTTTTATTAA ATAAATTGGA TGACACAGAA AATGCTAGTG CTTATGCAGC AAATGCAGGT
421     GTGGATAATA GAGAATGTAT ATCTATGGAT TACAAACAAA CACAATTGTG TTTAATTGGT
481     TGCAAACCAC CTATAGGGGA ACACTGGGGC AAAGGATCCC CATGTACCAA TGTTGCAGTA
541     AATCCAGGTG ATTGTCCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGC CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAAGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAT TAGTGGAAGA AACTAGTTTT
1261    ATTGATGCTG GTGCACCAGC TTGTCAAAAA CATACACCTC CAGCACCTAA AGAAGATCCC
1321    CTTAAAAAAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCCAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 11 (SEQ ID NO: 10)

```
Translation of ChiF(1-1518)
Universal code
Total amino acid number: 505, MW=56032
Max ORF: 1-1515, 505 AA, MW=56032

ORIGIN
1       MSLWLPSEAT VYLPPVPVSK VVSTDEYVAR TNIYYHAGTS RLLAVGHPYF PIKKPNNNKI
61      LVPKVSGLQY RVFRIHLPDP NKFGFPDTSF YNPDTQRLVW ACVGVEVGRG QPLGVGISGH
121     PLLNKLDDTE NASAYAANAG VDNRECISMD YKQTQLCLIG CKPPIGEHWG KGSPCTNVAV
181     NPGDCPPLEL INTVIQDGDM VDTGFGAMDF TTLQANKSEV PLDICTSICK YPDYIKMVSE
241     PYGDSLFFYL RREQMFVRHL FNRAGTVGEN VPDDLYIKGS GSTANLASSN YFPTPSGSMV
301     TSDAQIFNKP YWLQRAQGHN NGICWGNQLF VTVVDTTRST NMSLCAAIST SETTYKNTNF
361     KEYLRHGEEY DLQFIFQLCK ITLTADVMTY IHSMNSTILE DWNFGLQPPP GGTLVEETSF
421     IDAGAPACQK HTPPAPKEDP LKKYTFWEVN LKEKFSADLD QFPLGRKFLL QAGLKAKPKF
481     TLGKRKATPT TSSTSTTAKR KKRKL*
```

Figure 12 (SEQ ID NO: 11)

```
SEQ  Sa-hopt: 1518 bp;
Composition  486  A;  290  C;  293  G;  449  T;  0 OTHER
Percentage:   32%  A;  19%  C;  19%  G;  30%  T;  0%OTHER Molecular Weight (kDa):  ssDNA: 468.82    dsDNA: 935.7
ORIGIN
1      ATGTCTCTTT GGCTGCCTAG TGAGGCCACT GTCTACTTGC CTCCTGTCCC AGTATCTAAG
61     GTTGTAAGCA CGGATGAATA TGTTGCACGC ACAAACATAT ATTATCATGC AGGGACATCC
121    AGACTACTTG CAGTTGGACA TCCCTATTTT CCTATTAAAA AACCTAACAA TAACAAAATA
181    TTAGTTCCTA AAGTATCAGG ATTACAATAC AGGGTATTTA GAATACATTT ACCTGACCCC
241    TTAGTGGAAG AAACTAGTTT TATTGATGCT GGTGCACCAG ATACACAGCG GCTGGTTTGG
301    GCCTGTGTAG GTGTTGAGGT AGGCCGTGGT CAGCCATTAG GTGTGGGCAT TAGTGGCCAT
361    CCTTTATTAA ATAAATTGGA TGACACAGAA AATGCTAGTG CTTATGCAGC AAATGCAGGT
421    GTGGATAATA GAGAATGTAT ATCTATGGAT TACAAACAAA CACAATTGTG TTTAATTGGT
481    TGCAAACCAC CTATAGGGGA ACACTGGGGC AAAGGATCCC CATGTACCAA TGTTGCAGTA
541    AATCCAGGTG ATTGTCCACC ATTAGAGTTA ATAAACACAG TTATTCAGGA TGGTGATATG
601    GTTGATACTG GCTTTGGTGC TATGGACTTT ACTACATTAC AGGCTAACAA AAGTGAAGTT
661    CCACTGGATA TTTGTACATC TATTTGCAAA TATCCAGATT ATATTAAAAT GGTGTCAGAA
721    CCATATGGCG ACAGCTTATT TTTTTATTTA CGGAGGGAAC AAATGTTTGT TAGACATTTA
781    TTTAATAGGG CTGGTACTGT TGGTGAAAAT GTACCAGACG ATTTATACAT TAAAGGCTCT
841    GGGTCTACTG CAAATTTAGC CAGTTCAAAT TATTTTCCTA CACCTAGTGG TTCTATGGTT
901    ACCTCTGATG CCCAAATATT CAATAAACCT TATTGGTTAC AACGAGCACA GGGCCACAAT
961    AATGGCATTT GTTGGGGTAA CCAACTATTT GTTACTGTTG TTGATACTAC ACGCAGTACA
1021   AATATGTCAT TATGTGCTGC CATATCTACT TCAGAAACTA CATATAAAAA TACTAACTTT
1081   AAGGAGTACC TACGACATGG GGAGGAATAT GATTTACAGT TTATTTTTCA ACTGTGCAAA
1141   ATAACCTTAA CTGCAGACGT TATGACATAC ATACATTCTA TGAATTCCAC TATTTTGGAG
1201   GACTGGAATT TTGGTCTACA ACCTCCCCCA GGAGGCACAC TAGAAGATAC TTATAGGTTT
1261   GTAACATCCC AGGCAATTGC TTGTCAAAAA CATACACCTC CAGCACCTAA AGAAGATCCC
1321   CTTAAAAAAT ACACTTTTTG GGAAGTAAAT TTAAAGGAAA AGTTTTCTGC AGACCTAGAT
1381   CAGTTTCCTT TAGGACGCAA ATTTTTACTA CAAGCAGGAT TGAAGGCCAA ACCAAAATTT
1441   ACATTAGGAA AACGAAAAGC TACACCCACC ACCTCATCTA CCTCTACAAC TGCTAAACGC
1501   AAAAAACGTA AGCTGTAA
```

Figure 13 (SEQ ID NO: 12)

```
Translation of ChiH(1-1518)
Universal code
Total amino acid number: 505, MW=56041
Max ORF: 1-1515, 505 AA, MW=56041

ORIGIN
1      MSLWLPSEAT VYLPPVPVSK VVSTDEYVAR TNIYYHAGTS RLLAVGHPYF PIKKPNNNKI
61     LVPKVSGLQY RVFRIHLPDP LVEETSFIDA GAPDTQRLVW ACVGVEVGRG QPLGVGISGH
121    PLLNKLDDTE NASAYAANAG VDNRECISMD YKQTQLCLIG CKPPIGEHWG KGSPCTNVAV
181    NPGDCPPLEL INTVIQDGDM VDTGFGAMDF TTLQANKSEV PLDICTSICK YPDYIKMVSE
241    PYGDSLFFYL RREQMFVRHL FNRAGTVGEN VPDDLYIKGS GSTANLASSN YFPTPSGSMV
301    TSDAQIFNKP YWLQRAQGHN NGICWGNQLF VTVVDTTRST NMSLCAAIST SETTYKNTNF
361    KEYLRHGEEY DLQFIFQLCK ITLTADVMTY IHSMNSTILE DWNFGLQPPP GGTLEDTYRF
421    VTSQAIACQK HTPPAPKEDP LKKYTFWEVN LKEKFSADLD QFPLGRKFLL QAGLKAKPKF
481    TLGKRKATPT TSSTSTTAKR KKRKL*
```

Figure 14 (SEQ ID NO: 13)

"Dates" on the horizontal axis indicates "Time after inoculation (weeks)" and 6-Feb is the date of inoculation. "OD" on the vertical axis indicates "Optical Density".

TTAGTGGAAG AAACTAGTTT TATTGATGCT GGTGCACCA

Figure 27 (SEQ ID NO: 14)

LVEETSFIDA GAP

Figure 28 (SEQ ID NO: 1)

US 8,163,557 B2

CHIMAERIC HUMAN PAPILLOMAVIRUS 16 L1 VIRUS-LIKE PARTICLES AND A METHOD FOR PREPARING THE PARTICLES

BACKGROUND OF THE INVENTION

The invention relates to a method for preparing polypeptides, and in particular virus-like particles (VLPs) or capsomers of human papillomavirus.

The papillomaviruses are a group of small DNA viruses, which induce warts and other lesions in a variety of higher vertebrates including humans.

Papillomaviruses (PV) are members of the genus Papillomavirus, family Papillomaviridae, and contain a double stranded circular DNA genome with a typical size of 7 900 base pairs (Seedorf et al., 1985). All PVs have a similar genomic organisation, with an early gene region encoding proteins involved in DNA replication and cellular transformation, and a late region encoding the viral capsid proteins (FIG. 1). A non-coding region known as the long control region (LCR) contains control elements for transcription and replication.

Papillomaviruses encode two viral structural proteins, L1 and L2. The virion contains 360 L1 molecules arranged as 72 capsomers, each of which is a pentamer composed of five L1 molecules (Baker et al., 1991). The ratio of L1 to L2 molecules has been estimated as approximately 30:1 (Doobar et al., 1987), which suggests that each virion would contain approximately twelve L2 molecules. The greater number of L1 molecules per virion has led to L1 being referred to as the 'major' capsid protein and L2 being referred to as the 'minor' capsid protein.

HPV-16 L1 is encoded by a 1.518 kb gene, giving rise to a protein of 504 amino acids. L1 has a molecular weight of 55 to 58 kD (Browne et al., 1988). Domains of L1 are likely to mediate cell binding and to contain antigenic determinants mediating antibody and T cell immune responses to the virus.

Among the genital human papillomaviruses (HPVs), there are low risk HPVs (for example, HPV 6 and HPV 11) that cause genital warts and cervical lesions that usually regress or do not progress to malignancy, and high risk (or oncogenic) genotypes (for example, HPV 16 and HPV 18), which are associated with high-grade cervical lesions and carcinomas. HPVs have also been implicated as the etiological agents in several other anogenital and upper aerodigestive tract cancers (Breitburd et al., 1999). A compelling body of clinical, molecular, experimental and epidemiological evidence has established that certain HPV types are the main cause of cervical cancer (Lowy et al., 1994; IARC, 1995).

HPV 16 is present in most cases of cervical cancer cases and an additional three types (HPV 18, 31 and 45) are present in approximately an additional 30% of cases (IARC, 1999).

Although the incidence of cervical cancer is decreasing in the US, it is the most common malignancy in women in developing countries, with about 500 000 new cases diagnosed each year.

Traditionally most prophylactic vaccines have consisted of live, attenuated virus or formalin inactivated virus. Papillomavirus virions are highly immunogenic, inducing high titres (>10 000) of neutralising antibodies when systemically inoculated (Doretzky et al., 1980; Kirnbauer et al., 1991, 1992). However, due to the difficulties and risks involved in generating large quantities of these traditional vaccines there has been great emphasis on the development of viral protein subunit or virus-like particle (VLP) vaccines.

The best candidate protein for a prophylactic vaccine against HPV is the major capsid protein L1, which self-assembles into VLPs (Schiller and Lowy, 2001). These VLPs are very well characterised, and morphologically appear indistinguishable from whole virions (Chen et al., 2001; Rose et al., 1993). Injection of VLPs into experimental animals induces neutralising antibodies (Rose et al., 1998); preliminary human trials of injected VLP vaccines have also shown that these are well tolerated and highly immunogenic, and in the former case, stimulated robust B and T cell responses (Evans et al., 2001; Harro et al., 2001).

An effective, cheap prophylactic vaccine against oncogenic types of mucotropic HPVs could potentially have an impact on the world cancer burden, especially against HPV 16.

A common-neutralizing epitope for HPV types 6 and 16 has been found in the region (aa) 108-120 of the HPV 16 minor capsid protein, L2 (Kawana et al., 1998, 1999). Balb/c mice that were nasally immunised with a synthetic peptide corresponding to the epitope elicited an immune response that resulted in IgA and IgG antibodies cross-reacting with L1/L2 capsids of HPV 6, 16 and 18 (Kawana et al., 2001). Immunisation of rabbits with either of two overlapping peptides derived from the L2 sequence region 94-122 from either Rabbit oral papillomavirus (ROPV) or Cottontail rabbit papillomavirus (CRPV) resulted in sera which reacted to purified cognate L2, specifically recognised L2 in infected cells, and neutralised virus in vitro. Rabbits immunised with CRPV peptides were immune to CRPV challenge (Embers et al., 2002).

The inventors therefore decided to further investigate the presentation of this L2 epitope on chimaeric L1 VLPs as a vaccine in its own right, and as a model for the presentation of other immunogenic peptide sequences.

SUMMARY OF THE INVENTION

According to a first embodiment of the invention, there is provided a method for producing a chimaeric human papillomavirus (HPV) L1 polypeptide containing a HPV L2 peptide, the method comprising the steps of:
- introducing a DNA sequence coding for the L2 peptide into a DNA sequence coding for the L1 polypeptide;
- introducing the DNA sequence including the sequences for the L1 polypeptide and L2 peptide into a host cell in which the DNA sequence can be expressed;
- causing expression of the DNA sequence; and
- recovering the resulting chimaeric L1 polypeptide which includes the L2 peptide.

The HPV L1 polypeptide and/or HPV L2 peptide may be a HPV-16 polypeptide or peptide.

The HPV L2 peptide may have the following amino acid sequence: LVEETSFIDAGAP (SEQ ID NO: 1), or a sequence which is modification or derivative thereof, with the proviso that the modified or derived sequence is a sequence which has at least 80% homology to the sequence of SEQ ID NO: 1 and codes for a peptide which elicits an immunogenic response against HPV.

One or more nucleotides of the L1 DNA sequence may be deleted at the point of introduction of the L2 DNA sequence, and typically the number of nucleotides deleted from the L1 sequence will correspond with the number of L2 nucleotides inserted.

The expression of the protein could either be in a prokaryotic or eukaryotic expression system.

The chimaeric polypeptide may have the amino acid sequence set out in any one of FIGS. 6, 8, 10, 12 and 14 (SEQ ID NOs: 5, 7, 9, 11 and 13), or a sequence which is at least 80% homologous to any one of the sequences set out in SEQ ID NOs: 5, 7, 9, 11 and 13 and which is capable of eliciting an immunogenic response against HPV. The DNA sequence coding for the chimaeric polypeptide may be the DNA sequence as set out in any one of FIGS. 5, 7, 9, 11 and 13 (SEQ ID NOs: 4, 6, 8, 10 and 12), or a sequence having at least 80% homology to any one of these sequences and which codes for a polypeptide capable of eliciting an immunogenic response against HPV.

The chimaeric L1 polypeptide may assemble into virus-like particles and/or capsomers. The virus-like particle or capsomer may be immunogenic.

According to a second embodiment of the invention, there is provided a chimaeric HPV L1 DNA sequence into which the DNA sequence coding for the above HPV L2 peptide has been inserted, the resulting HPV L1 sequence being capable of expressing the HPV L2 peptide.

One or more nucleotides of the L1 DNA sequence at the point of introduction of the L2 DNA sequence may be deleted, and typically the number of nucleotides deleted from the L1 sequence will correspond with the number of L2 nucleotides inserted.

The chimaeric nucleic acid sequence may be a sequence as set out in any one of FIGS. 5, 7, 9, 11 and 13, or a DNA sequence which is a modification or derivative thereof, with the proviso that the modified or derived DNA sequence has at least 80% homology to any one of the sequences of SEQ ID NOs: 4, 6, 8, 10 and 12 and codes for a chimaeric L1 peptide which is capable of eliciting an immunogenic response against HPV.

According to a third embodiment of the invention, there is provided a vector including the nucleic acid sequence described above.

According to a fourth embodiment of the invention, there is provided a host cell including the vector described above.

According to yet a further embodiment of the invention, there is provided a chimaeric HPV L1 polypeptide that includes the above HPV L2 peptide (SEQ ID NO: 1).

The chimaeric polypeptide may be a chimaeric HPV L1 virus-like particle or capsomer.

According to a further embodiment of the invention, there is provided an HPV polypeptide having the amino acid sequence set out in any one of FIGS. 6, 8, 10, 12 and 14 (SEQ ID NOs: 5, 7, 9, 11 and 13), or a sequence which is a modification or derivative thereof, the modification or derivative being a sequence which is at least 80% homologous to any one of the sequences set out in SEQ ID NOs: 5, 7, 9, 11 and 13 and which is capable of eliciting an immunogenic response against HPV.

According to another embodiment of the invention, there is provided a method for producing a chimaeric human papillomavirus (HPV) L1 polypeptide containing a heterologous peptide, the method comprising the steps of:
  introducing a DNA sequence coding for the heterologous peptide into a DNA sequence coding for the L1 polypeptide;
  introducing the DNA sequence including the sequences for the L1 polypeptide and heterologous peptide into a host cell in which the DNA sequence can be expressed;
  causing expression of the DNA sequence; and
  recovering the resulting chimaeric L1 polypeptide which includes the heterologous peptide.

The heterologous peptide sequence may be any other HPV sequence, or may be derived from any antigenic epitope, B-cell or T-cell specific.

One or more nucleotides of the L1 DNA sequence at the point of introduction of the heterologous DNA sequence may be deleted, and typically the number of nucleotides deleted from the L1 sequence will correspond with the number of heterologous nucleotides inserted.

According to yet a further embodiment of the invention, there is provided a vaccine including the chimaeric HPV L1 polypeptide or a DNA sequence coding for the polypeptide, substantially as described above. The vaccine may be for prophylactic or therapeutic treatment of HPV infection, in particular HPV 6, 16 and 18.

Preferably, the vaccine will be capable of inducing an immunogenic response to HPV and to the introduced peptide in a suitable host.

The vaccine may further include a pharmaceutical excipient and/or adjuvant.

DESCRIPTION OF THE DRAWINGS

FIG. 2 shows the monomer structure of HPV 16 L1;

FIG. 3 shows the nucleotide sequence of the native sequence of the HPV 16 L1 gene into which the L2 epitope was inserted to produce the chimaeric constructs of FIGS. 5 to 14 (SEQ ID NO: 2);

FIG. 4 shows the amino acid sequence of FIG. 3 (SEQ ID NO: 3);

FIG. 5 shows the nucleotide sequence of chimaeric construct A (SEQ ID NO: 4);

FIG. 6 shows the amino acid sequence of chimaeric construct A (SEQ ID NO: 5);

FIG. 7 shows the nucleotide sequence of chimaeric construct C (SEQ ID NO: 6);

FIG. 8 shows the amino acid sequence of chimaeric construct C (SEQ ID NO: 7);

FIG. 9 shows the nucleotide sequence of chimaeric construct E (SEQ ID NO: 8);

FIG. 10 shows the amino acid sequence of chimaeric construct E (SEQ ID NO: 9);

FIG. 11 shows the nucleotide sequence of chimaeric construct F (SEQ ID NO: 10);

FIG. 12 shows the amino acid sequence of chimaeric construct F (SEQ ID NO: 11);

FIG. 13 shows the nucleotide sequence of chimaeric construct H (SEQ ID NO: 12);

FIG. 14 shows the amino acid sequence of chimaeric construct H (SEQ ID NO: 13);

FIG. 27 shows the nucleotide sequence of the L2 peptide which was inserted into the L1 sequence (SEQ ID NO: 14); and FIG. 28 shows the amino acid sequence of the L2 peptide which was inserted into the L1 sequence (SEQ ID NO: 1).

DETAILED DESCRIPTION OF AN EMBODIMENT OF THE INVENTION

Design of Chimaeric Constructs

Primers encoding the peptide:

LVEETSFIDAGAP (SEQ ID NO: 1)

which is a common-neutralising epitope for HPV 6 and 16 in the region (aa) 108-120 of the HPV minor capsid protein, L2, were synthesised.

According to the HPV 16 L1 monomer structure published by Chen et al. (2000) (FIG. 2), various surface loops and regions are exposed when pentamers and high order structures are formed.

Based on the epitope mapping of the V5 antibody (neutralising antibody raised to L1), various regions/loops were selected for the insertion of the L2 peptide so as to maintain the V5 antibody binding region of the L1 VLPs.

The major antigenic region (V5 binding region) of the L1 molecule has been mapped with amino acid residues A266, (with F50 being located beneath the surface residue V271) and S282 (Roden et al., 1996, White et al., 1999). Based on these residues, the inventors decided not to alter the B loop of the molecule, as this would alter the antigenic region and possibly destroy vital L1 epitopes.

The following L1 regions were therefore selected for insertion of the L2 peptide:

A: E-F loop
C: D-E loop
E: region between the h4 helix and J region of L1
F: h4 helix
H: internal C-D loop Synthesis of Chimaeric Constructs Chimaeric constructs were prepared by PCR with the primers being designed with the 3' end coding for the L2 peptide. The HPV 16 SA-opt L1 gene (FIGS. 3 and 4) cloned in the pSK plasmid vector was used as a template. The following DNA sequence was used to encode the L2 peptide:

(SEQ ID NO: 14)
5'-TTAGTGGAAGAAACTAGTTTTATTGATGCTGGTGCACCA-3'.

The L2 peptide was inserted into the gene by replacing the regions shown in Table 1. This method of replacing the existing nucleotides, rather than merely inserting the L2 nucleotides into the L1 sequence without any replacement, is advantageous in that disturbances of the tertiary structure are kept to a minimum, and the possibility of steric effects or interference with antibody binding to nearby sequences due to extra peptide "loops" is minimised.

Figure 1:
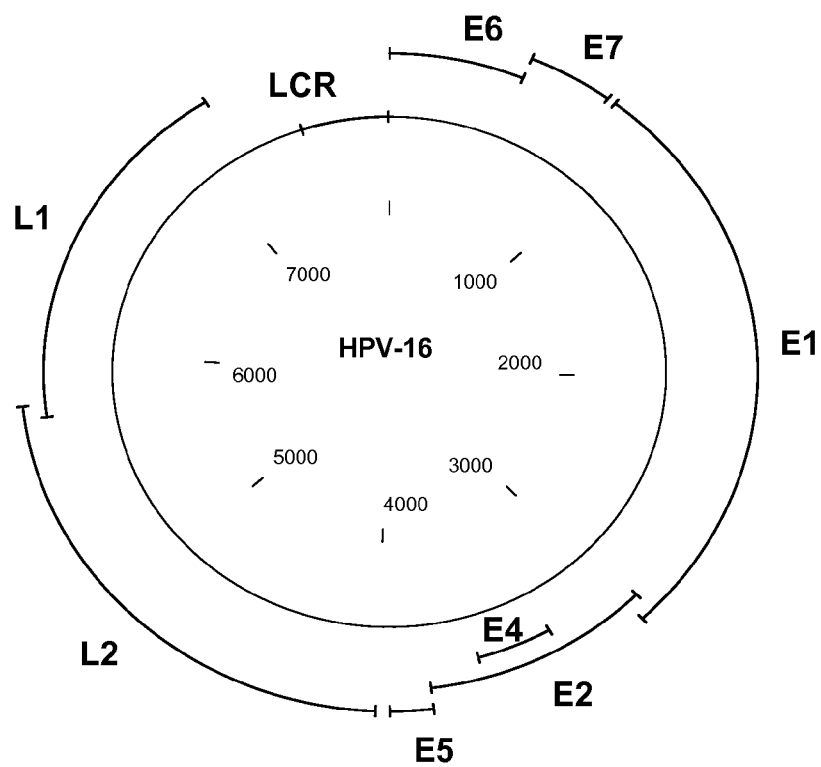
FIG. 1 shows a diagrammatic representation of the genomic organisation of HPV 16.
Figure 15:
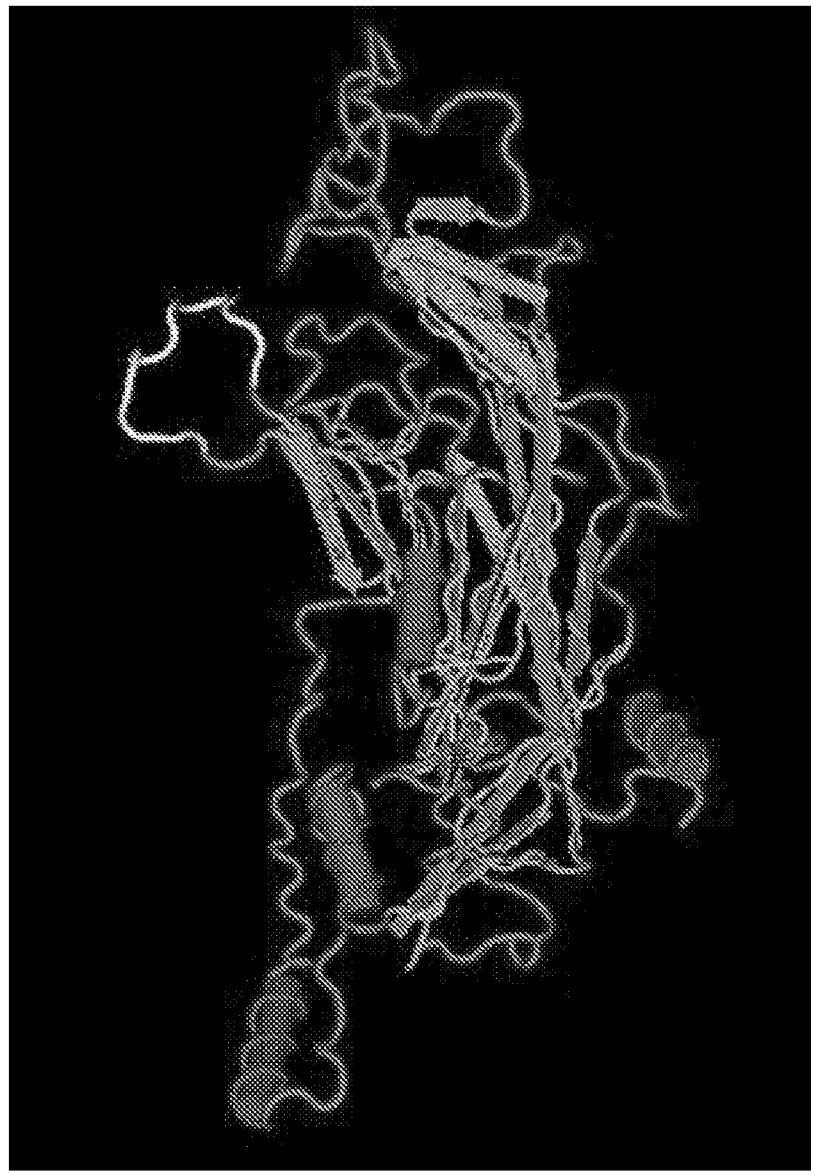
FIG. 15 shows a diagrammatic representation of the chimaeric construct A.
Figure 16:
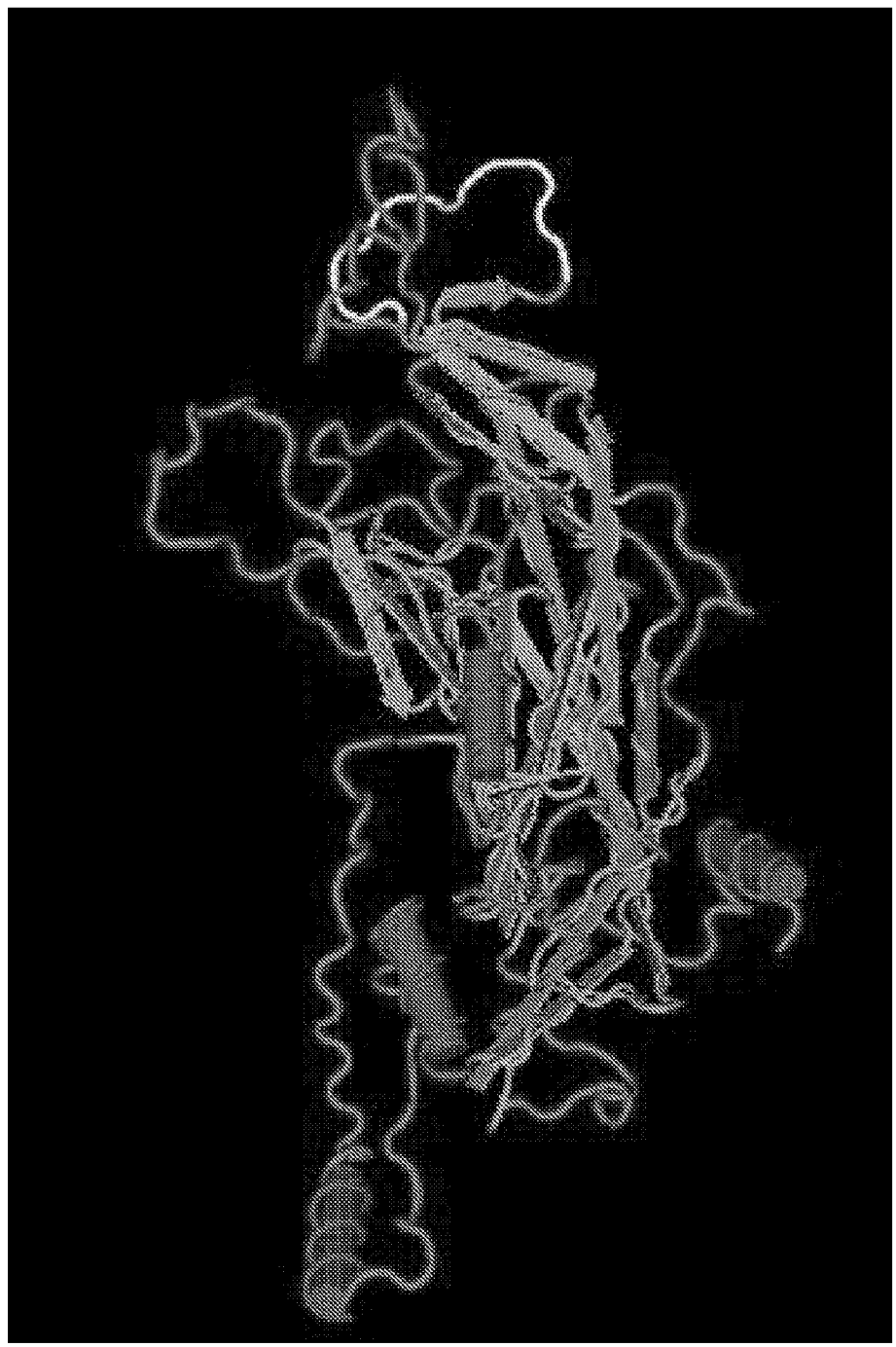
FIG. 16 shows a diagrammatic representation of the chimaeric construct C.
Figure 17:
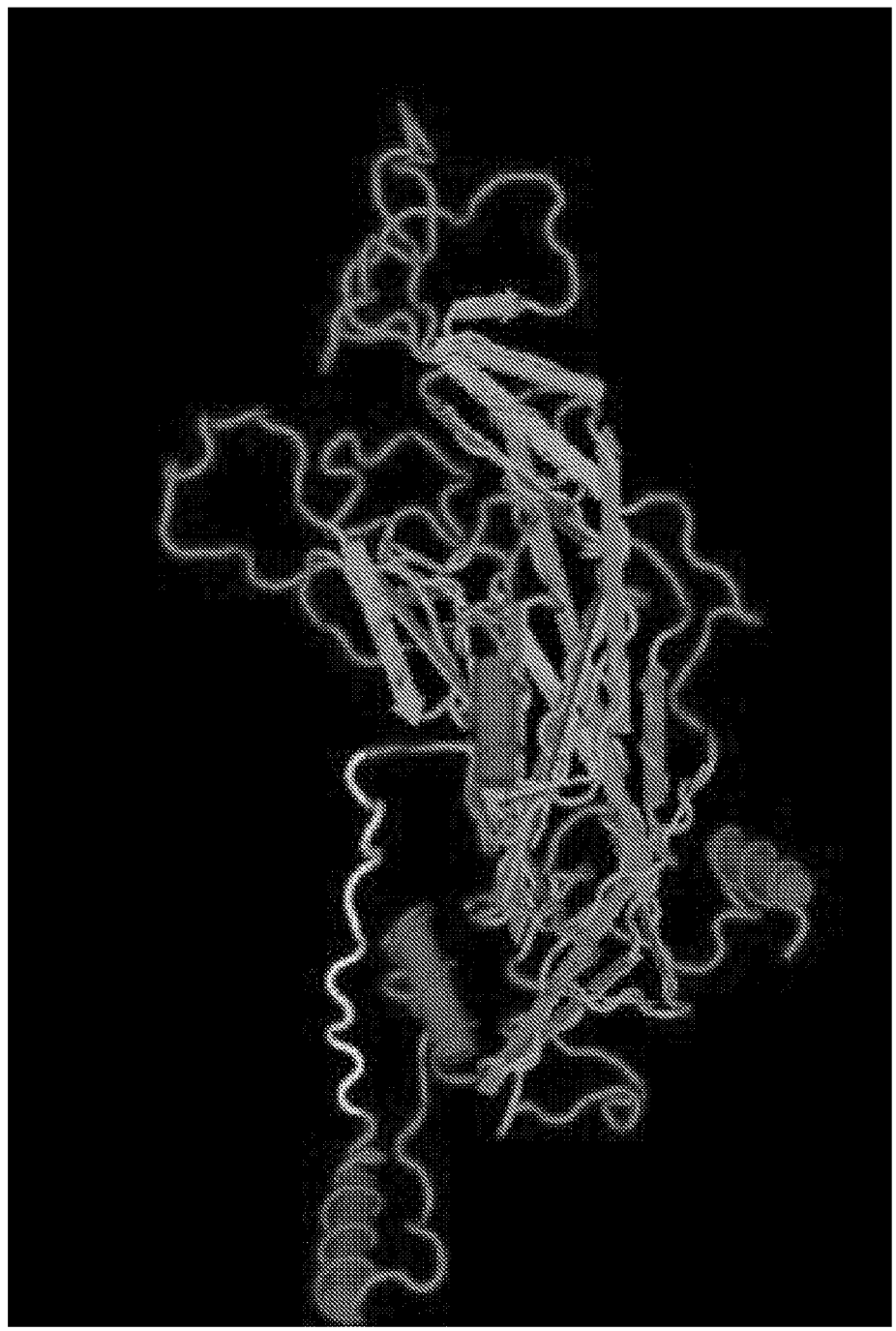
FIG. 17 shows a diagrammatic representation of the chimaeric construct E.
Figure 18:
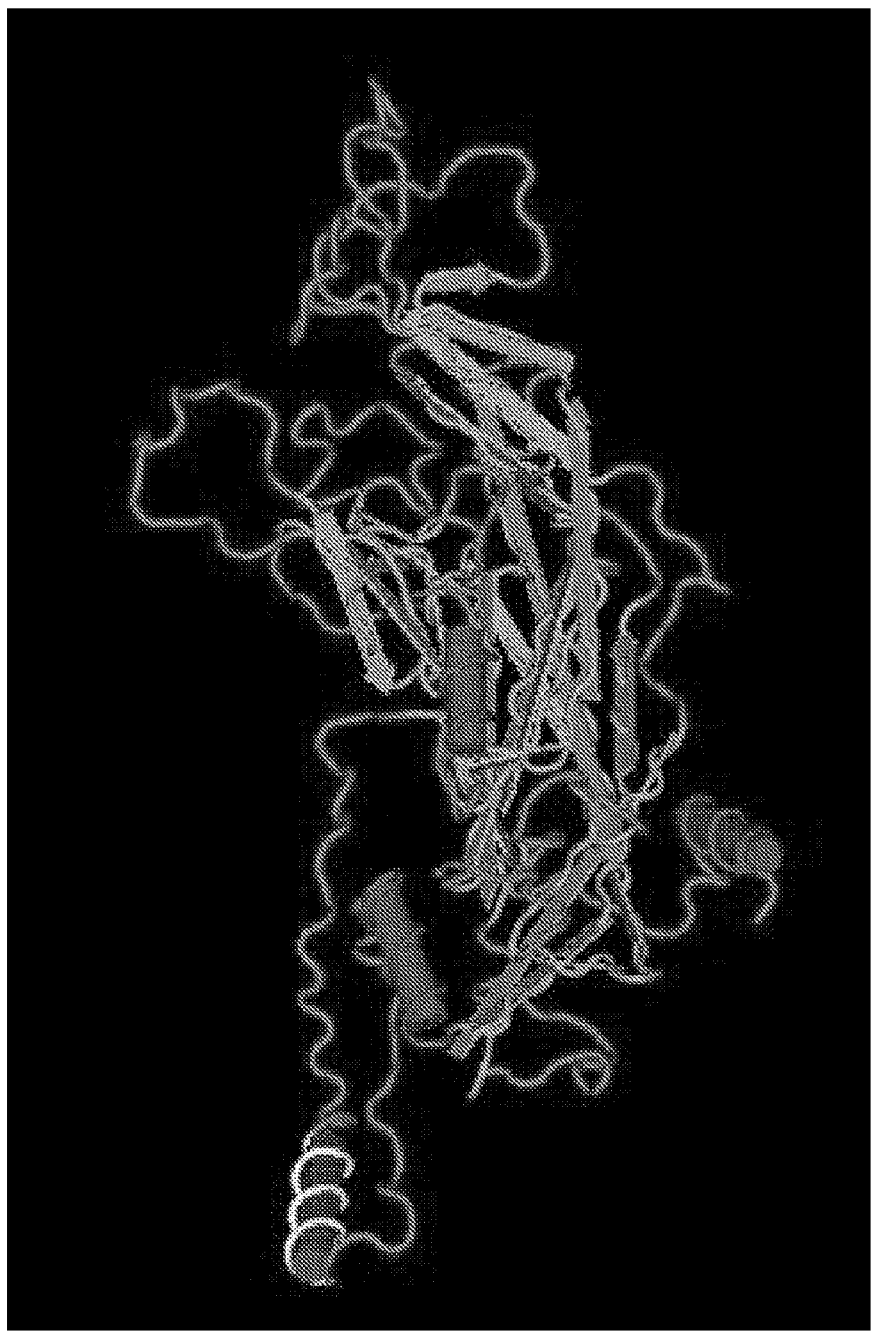
FIG. 18 shows a diagrammatic representation of the chimaeric construct F.
Figure 19:
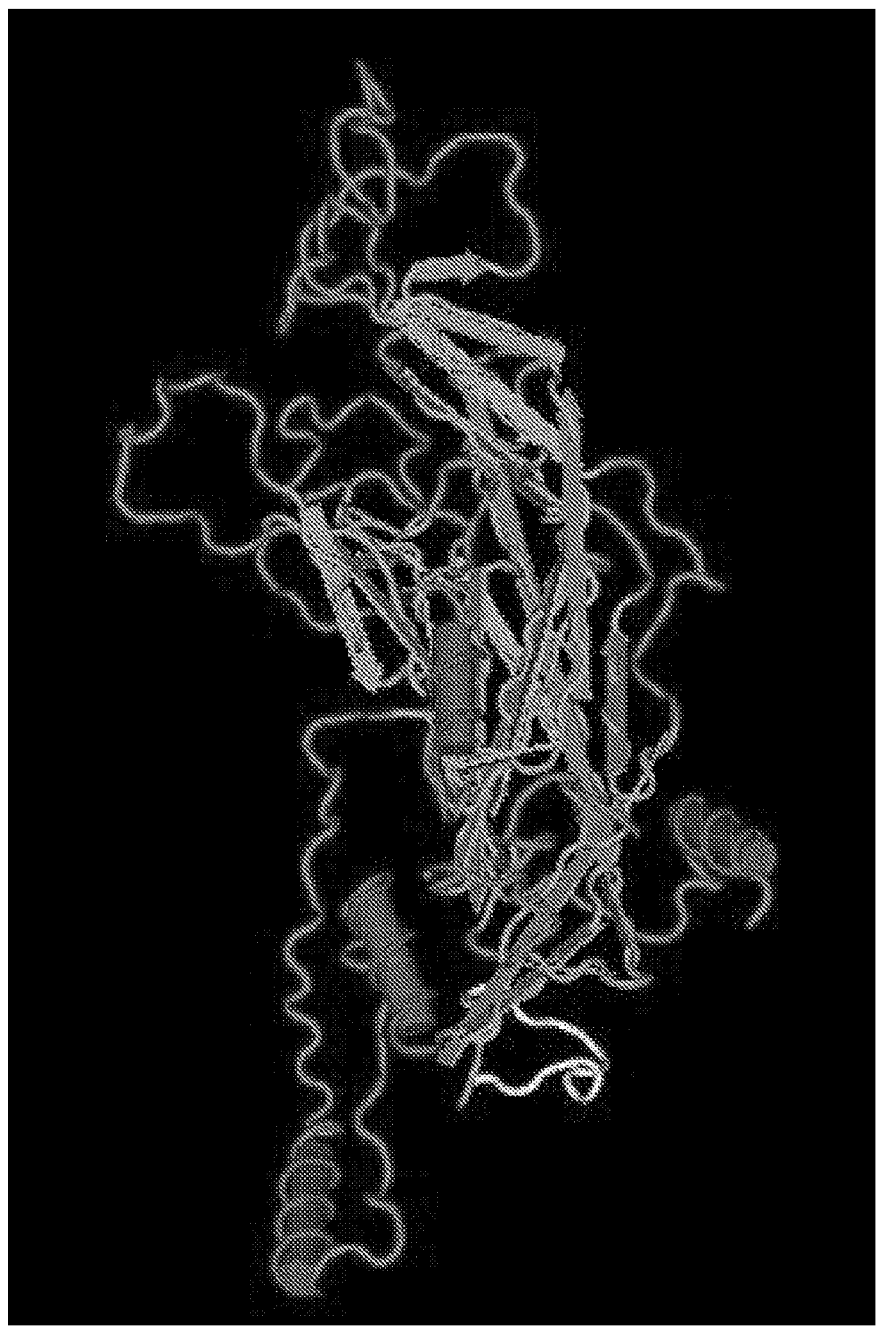
FIG. 19 shows a diagrammatic representation of the chimaeric construct H.

The position of the inserted L2 epitope is depicted for the chimaeric constructs in FIGS. 15 to 19 respectively.

The chimaeric genes from the sequenced pSK constructs were cloned into a pFastbac1 vector (Sal I/Xba I site). The DNA from the pFastbac1 clones was used to transfect DH10bac cells to prepare bacmid clones.

The chimaeric constructs were expressed in insect cells using the Bac-to-Bac® baculovirus expression system (Life Technologies).

TABLE 1

Insertion of L2 peptide

| Chimaeric construct | Nucleotide position of L2 peptide | Shown in FIG. No. (SEQ ID NO) | Amino acid position of L2 peptide | Shown in FIG. No. (SEQ ID NO) |
|---|---|---|---|---|
| A | 520-558 | FIG. No. 5 (SEQ ID NO: 4) | 174-186 | 6 (SEQ ID NO: 5) |
| C | 391-429 | FIG. No. 7 (SEQ ID NO: 6) | 131-143 | FIG. No. 8 (SEQ ID NO: 7) |
| E | 1291-1329 | FIG. No. 9 (SEQ ID NO: 8) | 431-443 | FIG. No. 10 (SEQ ID NO: 9) |
| F | 1240-1278 | FIG. No. 11 (SEQ ID NO: 10) | 414-426 | FIG. No. 12 (SEQ ID NO: 11) |
| H | 241-279 | FIG. No. 13 (SEQ ID NO: 12) | 81-93 | FIG. No. 14 (SEQ ID NO: 13) |

The bacmid DNA was transferred into sf21 (*Spodoptera frugiperda*) insect cells using cellfectin. The basic Bac-to-Bac® protocol was followed to amplify the recombinant virus and infect the sf21 insect cells for expression of the chimaeric VLPs.

A basic HPV 16 L1 VLP purification protocol was followed. The infected insect cells were spun down at 3 000 rpm and resuspended in phosphate buffered saline (PBS) with 0.5M NaCl. The suspension was sonicated 4 times at 5 second intervals. This was then overlayed onto a 40% sucrose cushion and pelleted at 100 000×g for 3 hrs. The pellet was resuspended in CsCl buffer (PBS with 0.4 g/ml CsCl) and resuspended by drawing up through 18 and 26 gauge needles to reduce the viscosity before sonication (4 times at 5 second intervals). The suspension was centrifuged at 100 000×g at 10° C. for 24 hrs.

No distinct bands were observed in CsCl gradients. 500 µl fractions were therefore collected and analysed by ELISA using conformation specific V5 and D9 (linear epitope) monoclonal antibodies. Fractions that were found to react to the V5 and/or D9 antibodies were pooled and dialysed against PBS at 4° C. overnight.

Results

Western blots showed that a polyclonal L2 antibody raised to the peptide in rabbits (obtained from Dr. Neil Christensen of The Jake Gittlen Cancer Research Institute, The Milton S. Hershey Medical Centre, Hershey Pa., USA) bound to the chimaeric L1 particles (55 kD), showing that the L2 epitope is expressed by the chimaeric constructs.

Antibody characterisation of the purified VLPs was carried out by ELISA using a panel of antibodies provided by Dr. Neil Christensen (Chistensen et al., 1996, 2001). Table 2 summarises the data.

TABLE 2

|   | V5 | E70 | U4 | 9A | D9 | I23 | L2 |
|---|---|---|---|---|---|---|---|
| A | + | − | + | + | + | + | + |
| C | − | − | + | + | + | + | + |
| E | + | + | + | + | + | + | + |

TABLE 2-continued

|      | V5 | E70 | U4 | 9A | D9 | I23 | L2 |
|------|----|-----|----|----|----|-----|-----|
| F    | +  | +   | +  | +  | +  | +   | +  |
| H    | -  | -   | -  | -  | +  | +   | +  |
| SA-opt | + | +  | +  | +  | -  | +   | -  |
| L1   |    |     |    |    |    |     |    |

A brief description of the antibodies and their binding regions is given in table 3 below.

TABLE 3

| V5 | Monoclonal, conformation specific antibody; aa 266 and 282 being critical |
| E70 | Monoclonal, conformation specific antibody; aa 50, 266 and 282 being critical |
| U4 | Monoclonal, conformation specific antibody |
| 9A | Monoclonal, binds a linear region in the are aa 1-171 |
| D9 | Monoclonal, binds denatured L1 protein |
| I23 | Monoclonal, binds in the region aa 111-130 |
| L2 | Polyclonal antibody that binding the L2 epitope (aa108-120) |

Electron Microscopy of the Chimaeric Particles

EM results showed that the particles formed from the chimaeric constructs are not identical to those produced by the wild type HPV L1 gene. The particles formed are mainly in a partially broken down or partially disassembled state and are generally seen to clump together Animal Experimentation with Chimaeric Antigen Six sets of 5 Balb/c mice were used for the animal experimentation to determine if inoculation with the chimaeric VLPs elicited an immune response. Chimaeric VLPs produced from the 5 chimaeric constructs and VLPs produced from a non-chimaeric HPV 16 L1 (SA-opt) were injected at a concentration of 100 µg at two sub-cutaneous sites. The animals were inoculated at weeks 0, 2 and 4. Blood samples and vaginal washes were taken at various time periods.

Figure 20:
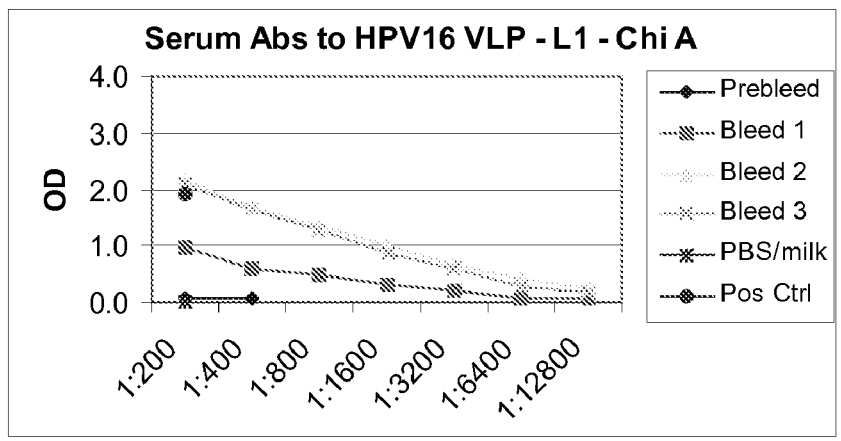
FIG. 20 shows data obtained from end point titrations of mice inoculated with chimaeric VLPs obtained from construct A.
Figure 21:
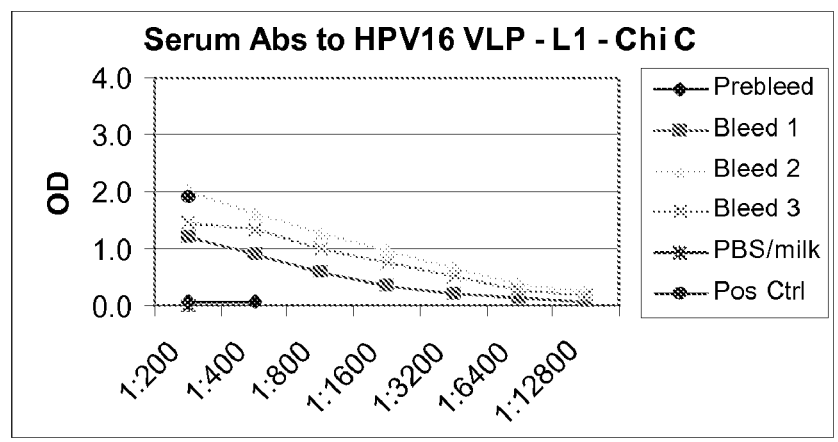
FIG. 21 shows data obtained from end point titrations of mice inoculated with chimaeric VLPs obtained from construct C.
Figure 22:
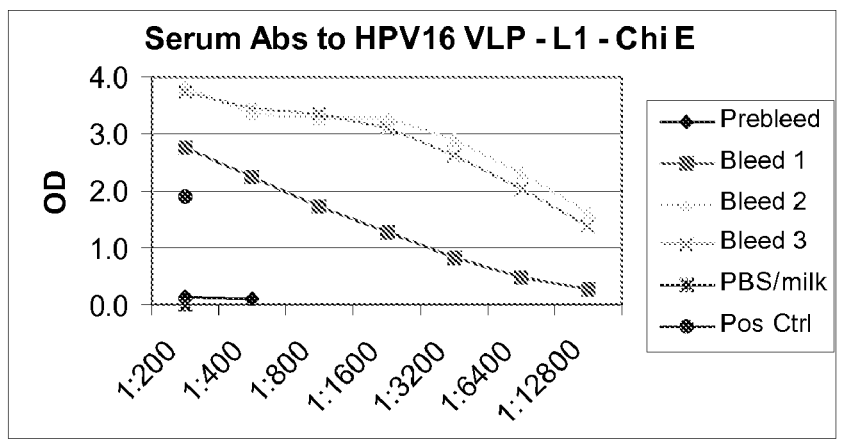
FIG. 22 shows data obtained from end point titrations of mice inoculated with chimaeric VLPs obtained from construct E.
Figure 23:
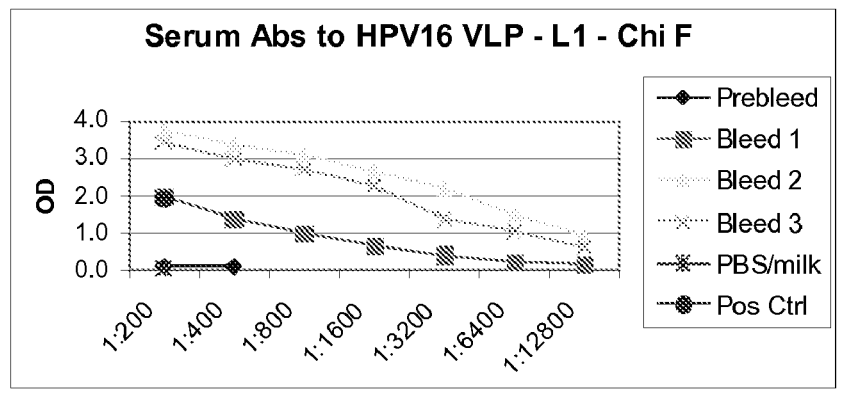
FIG. 23 shows data obtained from end point titrations of mice inoculated with chimaeric VLPs obtained from construct F.
Figure 24:
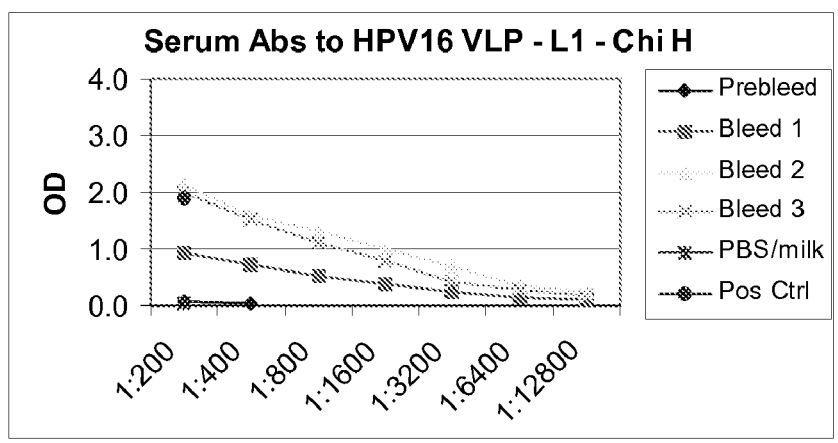
FIG. 24 shows data obtained from end point titrations of mice inoculated with chimaeric VLPs obtained from construct H.
Figure 25:
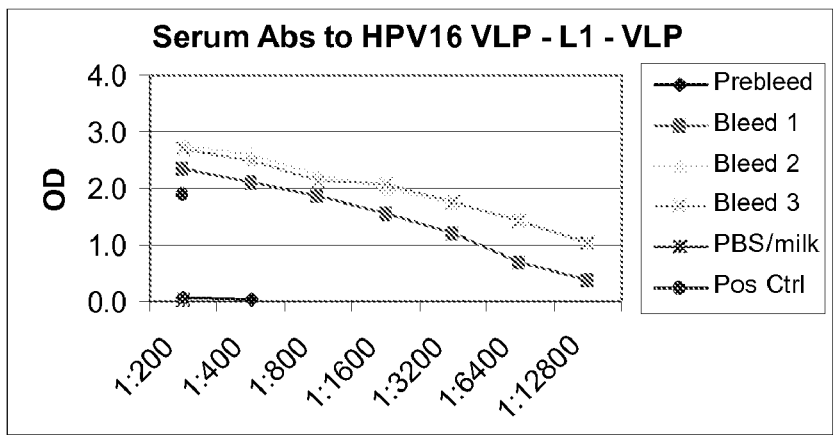
FIG. 25 shows data obtained from end point titrations of mice inoculated with VLPs obtained from a non-chimaeric HPV 16 L1 (SA-opt)
Figure 26:
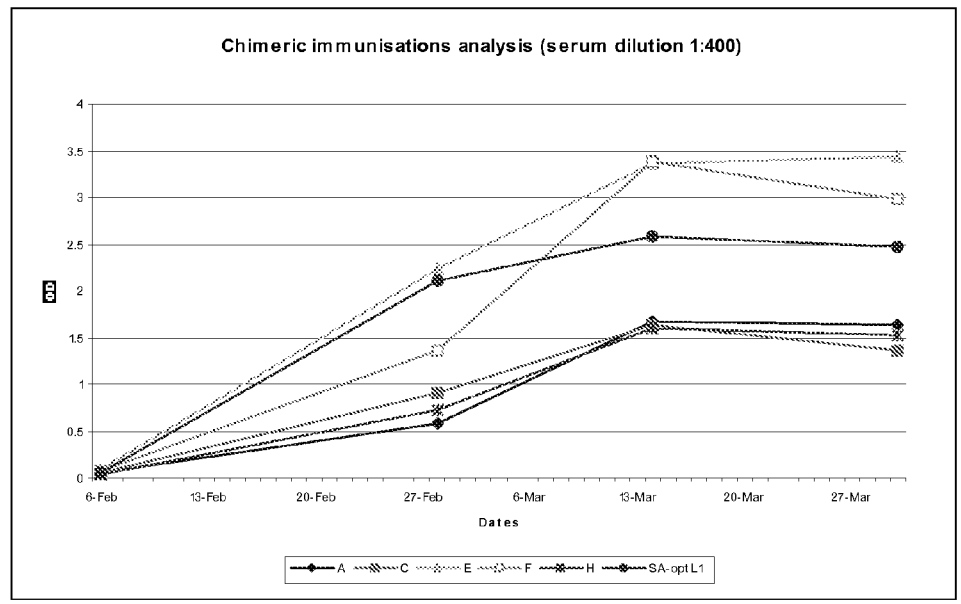
FIG. 26 shows the response of mice to boosters following initial immunisation.

The mouse sera from each group was pooled and analysed by ELISA using VLPs produced in insect cells by recombinant baculoviruses. End point titrations for each group of mice were carried out to determine the extent of the response and give a better reflection of the response (FIGS. 20 to 26).

The results indicate that a high immune response was achieved.

REFERENCES

Baker, T. S., W. W. Newcomb, N. H. Olson, L. M. Cowsert, C. Olson, and J. C. Brown. 1991. Biophys. J. 60:1445-1456.
Breitburd, F. and P. Coursaget. 1999. Cancer Biology 9:431-445.
Browne, H. M., M. J. Churcher, M. A. Stanley, G. L. Smith, and A. C. Minson. 1988. J. Gen. Virol. 69, 1263-1273.
Chen, X. S., Garcea, R. L., Goldberg, I., Casini, G., and Harrison, S. C. (2000). Mol Cell 5, 557-567.
Chen, X. S., Casini, G., Harrison, S. C and Garcea, R. (2001). Journal of Molecular Biology 307, 173-182.
Christensen, N. D., J. Diller, C. Eklund, J. J. Carter, G. C. Wipf, C. A. Reed, N. M. Cladel, and D. A. Galloway. 1996. Virol. 223, 174-184.
Christensen N D, Cladel N M, Reed C A, Budgeon L R, Embers M E, Skulsky D M, McClements W L, Ludmerer S W, Jansen K U. 2001. 20; 291(2):324-34.
Doorbaar, J., and P. H. Gallimore. 1987. J. Virol. 61:2793-2799.
Doretzky, I., R. Shober, S. K. Chattopadhyay, and D. R. Lowy. 1980. Virology 103:369-375.
M E Embers, L R Budgeon, M Pickel, N D Christensen. 2002. J. Virol., 76 (19): 9798-9805.
Evans, T. G., Bonnez, W., Rose, R. C., Koenig, S., Demeter, L., Suzich, J. A., O'Brien, D., Campbell, M., White, W. I., Balsley, J., and Reichman, R. C. 2001. J. Infect. Dis. 183, 1485-1493.
Harro, C. D., Pang, Y. Y., Roden, R. B., Hildesheim, A., Wang, Z., Reynolds, M. J., Mast, T. C., Robinson, R., Murphy, B. R., Karron, R. A., Dillner, J., Schiller, J. T., and Lowy, D. R. 2001. J. Natl. Cancer Inst. 93, 284-292.
IARC, World Health Organization. 1995. WHO Report of a technical meeting, Geneva. Ref Type: Report
IARC, World Health Organization. 1999. WHO. Report of a technical meeting, Geneva, 16-18 Feb. 1999. 1999. Ref Type: Report
Kawana, K., Matsumoto, K., Yoshikawa, H., Taketani, Y., Kawana, T., Yoshiike, K., and Kanda, T. 1998. Virology 245, 353-359.
Kawana, K., Yoshikawa, H., Takentani, Y., Yoshiike, K., and Kanda, T. (1999). Journal of Virology 73, 6188-6190.
Kawana, K., Kawana, Y., Yoshikawa, H., Takentani, Y., Yoshiike, K., and Kanda, T. (2001). Vaccine 19, 1496-1502.
Kirnbauer, R., F. Booy, N. Cheng, D. R. Lowy, and J. T. Schiller. 1992. Proc. Natl. Acad. Sci. USA. 89, 12180-12184.
Kirnbauer, R., J. Taub, H. Greenstone, R. Roden, M. Durst, L. Gissman, D. R. Lowy, and J. T. Schiller. 1993. J. Virol. 67, 6929-6936.
Lowy, D. R., R. Kirnbauer, and J. T. Schiller. 1994. Proc Natl Acad Sci USA 91:2436-2440.
Roden, R. B. S., H. L. Greenstone, R. Kirnbauer, F. P. Booy, J. Jessie, D. R. Lowy, and J. T. Schiller. 1996. J. Virol. 70, 5875-5883.
Rose, R. C., Bonnez, W., Reichman, R. C., and Garcea, R. L. 1993. J Virol 67, 1936-1944.
Rose, R. C., White, W. I., Li, M., Suzich, J. A., Lane, C., and Garcea, R. L. 1998. Journal of Virology 72, 6151-6154.
Schiller, J. T. and Lowy, D. R. 2001. Expert. Opin. Biol. Ther. 1, 571-581.
Seedorf, K., G. Krämmer, M. Dürst, S. Suhai, and W. G. Röwekamp. 1985. Virol. 145, 181-185.
White, W. I., Wilson, S. D., Palmer-Hill, F. J., Woods, R. M., Ghim, S.-J., Hewitt, L. A., Goldman, D. M., Burke, S. J., Jenson, A. B., Koenig, S., and Suzich, J. A. 1999. J. Virol. 73, 4882-488.

The invention claimed is:

1. A chimaeric human papillomavirus (HPV) sequence comprising an HPV L1 DNA sequence into which heterologous DNA sequence has been inserted at a region of a L1 polypeptide encoded by the HPV L1 DNA sequence, the region being selected from the group consisting of the E-F loop, the region between the h4 helix and J region of L1, the h4 helix, and the internal C-D loop, wherein the HPV L1 DNA sequence is capable of expressing the heterologous peptide.

2. The chimaeric HPV sequence according to claim 1, wherein the heterologous DNA sequence is a sequence encoding for a HPV L2 peptide (SEQ I.D. NO: 1).

3. The chimaeric HPV sequence according to claim 2, wherein one or more nucleotides of the L1 DNA sequence have been deleted at the point of introduction of the L2 DNA sequence.

4. The chimaeric HPV sequence according to claim 3, wherein the number of nucleotides deleted from the L1 sequence corresponds with the number of L2 nucleotides inserted.

5. A vector comprising the chimeric HPV sequence as described in claim 2.

6. An isolated host cell comprising the vector as claimed in claim 5.

7. The chimaeric HPV sequence according to claim 1, wherein the chimaeric HPV sequence has a DNA sequence set out in any one of SEQ ID NOs: 4, 6, 8, 10 and 12, or a DNA sequence which is a modification or derivative thereof, with the proviso that the modified or derived DNA sequence has at least 80% sequence identity to the insert region of any one of SEQ ID NOs: 4, 6, 8, 10 and 12 and encodes for a peptide being capable of eliciting an immunogenic response against HPV.

8. The chimaeric HPV DNA sequence according to claim 1, wherein the heterologous DNA sequence encodes a peptide having the amino acid sequence:

LVEETSFIDAGAP (SEQ ID NO:1).

9. A vector comprising the chimeric HPV sequence as described in claim 1.

10. An isolated host cell compromising the vector as claimed in claim 9.

* * * * *

SEQUENCE LISTING

```
<160> NUMBER OF SEQ ID NOS: 14

<210> SEQ ID NO 1
<211> LENGTH: 13
<212> TYPE: PRT
<213> ORGANISM: Human papillomavirus
```

<400> SEQUENCE: 1

Leu Val Glu Glu Thr Ser Phe Ile Asp Ala Gly Ala Pro
1               5                   10

<210> SEQ ID NO 2
<211> LENGTH: 1518
<212> TYPE: DNA
<213> ORGANISM: Human papillomavirus

<400> SEQUENCE: 2

| | | | | | |
|---|---|---|---|---|---|
| atgtctcttt | ggctgcctag | tgaggccact | gtctacttgc | ctcctgtccc | agtatctaag | 60 |
| gttgtaagca | cggatgaata | tgttgcacgc | acaaacatat | attatcatgc | agggacatcc | 120 |
| agactacttg | cagttggaca | tccctatttt | cctattaaaa | acctaacaa | taacaaaata | 180 |
| ttagttccta | agtatcagg | attacaatac | agggtattta | gaatacattt | acctgacccc | 240 |
| aataagtttg | gttttcctga | cacctcattt | tataatccag | atacacagcg | gctggtttgg | 300 |
| gcctgtgtag | gtgttgaggt | aggccgtggt | cagccattag | gtgtgggcat | tagtggccat | 360 |
| cctttattaa | ataaattgga | tgacacagaa | aatgctagtg | cttatgcagc | aaatgcaggt | 420 |
| gtggataata | gagaatgtat | atctatggat | tacaaacaaa | cacaattgtg | tttaattggt | 480 |
| tgcaaaccac | ctataggga | acactggggc | aaaggatccc | catgtaccaa | tgttgcagta | 540 |
| aatccaggtg | attgtccacc | attagagtta | ataaacacag | ttattcagga | tggtgatatg | 600 |
| gttgatactg | gctttggtgc | tatggacttt | actacattac | aggctaacaa | aagtgaagtt | 660 |
| ccactggata | tttgtacatc | tatttgcaaa | tatccagatt | atattaaaat | ggtgtcagaa | 720 |
| ccatatggcg | acagcttatt | tttttattta | cggagggaac | aaatgtttgt | tagacattta | 780 |
| tttaataggg | ctggtactgt | tggtgaaaat | gtaccagacg | atttatacat | taaaggctct | 840 |
| gggtctactg | caaatttagc | cagttcaaat | tattttccta | cacctagtgg | ttctatggtt | 900 |
| acctctgatg | cccaaatatt | caataaacct | tattggttac | aacgagcaca | gggccacaat | 960 |
| aatggcattt | gttgggggtaa | ccaactattt | gttactgttg | ttgatactac | acgcagtaca | 1020 |
| aatatgtcat | tatgtgctgc | catatctact | tcagaaacta | catataaaaa | tactaactt | 1080 |
| aaggagtacc | tacgacatgg | ggaggaatat | gatttacagt | ttattttca | actgtgcaaa | 1140 |
| ataaccttaa | ctgcagacgt | tatgacatac | atacattcta | tgaattccac | tattttggag | 1200 |
| gactggaatt | ttggtctaca | acctccccca | ggaggcacac | tagaagatac | ttataggttt | 1260 |
| gtaacatccc | aggcaattgc | ttgtcaaaaa | catacacctc | cagcacctaa | agaagatccc | 1320 |
| cttaaaaaat | acacttttg | ggaagtaaat | ttaaaggaaa | agttttctgc | agacctagat | 1380 |
| cagtttcctt | taggacgcaa | attttacta | caagcaggat | tgaaggccaa | accaaaattt | 1440 |
| acattaggaa | aacgaaaagc | tacacccacc | acctcatcta | cctctacaac | tgctaaacgc | 1500 |
| aaaaaacgta | agctgtaa | | | | | 1518 |

<210> SEQ ID NO 3
<211> LENGTH: 505
<212> TYPE: PRT
<213> ORGANISM: Human papillomavirus

<400> SEQUENCE: 3

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

-continued

```
Ile Tyr Tyr His Ala Gly Thr Ser Arg Leu Leu Ala Val Gly His Pro
             35                  40                  45

Tyr Phe Pro Ile Lys Lys Pro Asn Asn Asn Lys Ile Leu Val Pro Lys
 50                  55                  60

Val Ser Gly Leu Gln Tyr Arg Val Phe Arg Ile His Leu Pro Asp Pro
 65                  70                  75                  80

Asn Lys Phe Gly Phe Pro Asp Thr Ser Phe Tyr Asn Pro Asp Thr Gln
                 85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
            115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
            195                 200                 205

Asp Phe Thr Thr Leu Gln Ala Asn Lys Ser Glu Val Pro Leu Asp Ile
210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
435                 440                 445

Val Asn Leu Lys Glu Lys Phe Ser Ala Asp Leu Asp Gln Phe Pro Leu
450                 455                 460
```

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
        500                 505

<210> SEQ ID NO 4
<211> LENGTH: 1518
<212> TYPE: DNA
<213> ORGANISM: Human papillomavirus

<400> SEQUENCE: 4
atgtctcttt ggctgcctag tgaggccact gtctacttgc ctcctgtccc agtatctaag      60
gttgtaagca cggatgaata tgttgcacgc acaaacatat attatcatgc agggacatcc     120
agactacttg cagttggaca tcccattttt cctattaaaa aacctaacaa taacaaaata     180
ttagttccta aagtatcagg attacaatac agggtattta gaatacattt acctgacccc     240
aataagtttg gttttcctga cacctcattt tataatccag atacacagcg gctggtttgg     300
gcctgtgtag gtgttgaggt aggccgtggt cagccattag gtgtgggcat tagtggccat     360
cctttattaa ataaattgga tgacacagaa aatgctagtg cttatgcagc aaatgcaggt     420
gtggataata gagaatgtat atctatggat tacaaacaaa cacaattgtg tttaattggt     480
tgcaaaccac ctataggggga acactggggc aaaggatcct tagtggaaga aactagtttt     540
attgatgctg gtgcaccacc attagagtta ataaacacag ttattcagga tggtgatatg     600
gttgatactg gctttggtgc tatggacttt actacattac aggctaacaa agtgaagtt      660
ccactggata tttgtacatc tatttgcaaa tatccagatt atattaaaat ggtgtcagaa     720
ccatatggcg acagcttatt tttttattta cggagggaac aaatgtttgt tagacattta     780
tttaataggg ctggtactgt tggtgaaaat gtaccagacg atttatacat taaaggctct     840
gggtctactg caaatttagc cagttcaaat tattttccta cacctagtgg ttctatggtt     900
acctctgatg cccaaatatt caataaacct tattggttac aacgagcaca gggccacaat     960
aatggcattt gttgggggta accaactatt tgttactgttg ttgatactac acgcagtaca    1020
aatatgtcat tatgtgctgc catatctact tcagaaacta catataaaaa tactaacttt    1080
aaggagtacc tacgacatgg ggaggaatat gatttacagt ttatttttca actgtgcaaa    1140
ataaccttaa ctgcagacgt tatgacatac atacattcta tgaattccac tattttggag    1200
gactggaatt ttggtctaca acctccccca ggaggcacac tagaagatac ttataggttt    1260
gtaacatccc aggcaattgc ttgtcaaaaa catacacctc cagcacctaa gaagatccc     1320
cttaaaaaat acacttttgg ggaagtaaat ttaaaggaaa gttttctgc agacctagat     1380
cagtttcctt taggacgcaa attttttacta caagcaggat tgaaggccaa accaaaattt    1440
acattaggaa aacgaaaagc tacacccacc acctcatcta cctctacaac tgctaaacgc    1500
aaaaaacgta agctgtaa                                                   1518

<210> SEQ ID NO 5
<211> LENGTH: 505
<212> TYPE: PRT
<213> ORGANISM: Human papillomavirus

<400> SEQUENCE: 5

Met Ser Leu Trp Leu Pro Ser Glu Ala Thr Val Tyr Leu Pro Pro Val
1               5                   10                  15

-continued

Pro Val Ser Lys Val Ser Thr Asp Glu Tyr Val Ala Arg Thr Asn
         20                  25                  30

Ile Tyr Tyr His Ala Gly Thr Ser Arg Leu Leu Ala Val Gly His Pro
         35                  40                  45

Tyr Phe Pro Ile Lys Lys Pro Asn Asn Asn Lys Ile Leu Val Pro Lys
         50                  55                  60

Val Ser Gly Leu Gln Tyr Arg Val Phe Arg Ile His Leu Pro Asp Pro
 65                  70                  75                  80

Asn Lys Phe Gly Phe Pro Asp Thr Ser Phe Tyr Asn Pro Asp Thr Gln
                 85                  90                  95

Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
             115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Leu Val Glu
                165                 170                 175

Glu Thr Ser Phe Ile Asp Ala Gly Ala Pro Leu Glu Leu Ile Asn
             180                 185                 190

Thr Val Ile Gln Asp Gly Asp Met Val Asp Thr Gly Phe Gly Ala Met
         195                 200                 205

Asp Phe Thr Thr Leu Gln Ala Asn Lys Ser Glu Val Pro Leu Asp Ile
         210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
             260                 265                 270

Asp Asp Leu Tyr Ile Lys Gly Ser Gly Ser Thr Ala Asn Leu Ala Ser
         275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
             340                 345                 350

Thr Thr Tyr Lys Asn Thr Asn Phe Lys Glu Tyr Leu Arg His Gly Glu
         355                 360                 365

Glu Tyr Asp Leu Gln Phe Ile Phe Gln Leu Cys Lys Ile Thr Leu Thr
         370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
         420                 425                 430

Pro Pro Ala Pro Lys Glu Asp Pro Leu Lys Lys Tyr Thr Phe Trp Glu 435                 440                 445
Val Asn Leu Lys Glu Lys Phe Ser Ala Asp Leu Asp Gln Phe Pro Leu
            450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 6
<211> LENGTH: 1518
<212> TYPE: DNA
<213> ORGANISM: Human papillomavirus

<400> SEQUENCE: 6
atgtctcttt ggctgcctag tgaggccact gtctacttgc ctcctgtccc agtatctaag      60
gttgtaagca cggatgaata tgttgcacgc acaaacatat attatcatgc agggacatcc     120
agactacttg cagttggaca tccctatttt cctattaaaa aacctaacaa taacaaaata     180
ttagttccta agtatcagg attacaatac agggtattta gaatacattt acctgacccc      240
aataagtttg gttttcctga cacctcattt tataatccag atacacagcg gctggtttgg     300
gcctgtgtag gtgttgaggt aggccgtggt cagccattag gtgtgggcat tagtggccat     360
cctttattaa ataaattgga tgacacagaa ttagtggaag aaactagttt tattgatgct     420
ggtgcaccaa gagaatgtat atctatggat acaaacaaa cacaattgtg tttaattggt      480
tgcaaaccac ctataggga acactggggc aaaggatccc catgtaccaa tgttgcagta      540
aatccaggtg attgtccacc attagagtta ataaacacag ttattcagga tggtgatatg     600
gttgatactg gctttggtgc tatggactt actacattac aggctaacaa agtgaagtt      660 ccactggata tttgtacatc tatttgcaaa tatccagatt atattaaaat ggtgtcagaa     720
ccatatggcg acagcttatt ttttatttta cggagggaac aaatgtttgt tagacattta     780
tttaataggg ctggtactgt tggtgaaaat gtaccagacg atttatacat taaaggctct     840
gggtctactg caaatttagc cagttcaaat tattttccta cacctagtgg ttctatggtt     900
acctctgatg cccaaatatt caataaacct tattggttac aacgagcaca gggccacaat     960
aatggcattt gttgggggtaa ccaactattt gttactgttg ttgatactac acgcagtaca    1020
aatatgtcat tatgtgctgc catatctact tcagaaacta catataaaaa tactaacttt    1080
aaggagtacc tacgacatgg ggaggaatat gatttacagt ttatttttca actgtgcaaa    1140
ataaccttaa ctgcagacgt tatgacatac atacattcta tgaattccac tattttggag    1200
gactggaatt ttggtctaca acctcccca ggaggcacac tagaagatac ttataggttt     1260
gtaacatccc aggcaattgc ttgtcaaaaa catacacctc cagcacctaa gaagatccc    1320 cttaaaaaat acacttttg ggaagtaaat ttaaaggaaa gttttctgc agacctagat      1380 cagtttcctt taggacgcaa attttttacta caagcaggat tgaaggccaa accaaaattt   1440
acattaggaa aacgaaaagc tacacccacc acctcatcta cctctacaac tgctaaacgc   1500
aaaaaacgta agctgtaa                                                 1518

<210> SEQ ID NO 7
<211> LENGTH: 505
<212> TYPE: PRT
<213> ORGANISM: Human papillomavirus

<400> SEQUENCE: 7

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Leu Val Glu Glu Thr Ser Phe Ile Asp Ala Gly Ala Pro Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
            195                 200                 205

Asp Phe Thr Thr Leu Gln Ala Asn Lys Ser Glu Val Pro Leu Asp Ile
        210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
        370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415
```

```
Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 8
<211> LENGTH: 1518
<212> TYPE: DNA
<213> ORGANISM: Human papillomavirus

<400> SEQUENCE: 8
atgtctcttt ggctgcctag tgaggccact gtctacttgc ctcctgtccc agtatctaag      60
gttgtaagca cggatgaata tgttgcacgc acaaacatat attatcatgc agggacatcc     120
agactacttg cagttggaca tccctatttt cctattaaaa aacctaacaa taacaaaata     180
ttagttccta agtatcagg attacaatac agggtattta gaatacattt acctgacccc     240
aataagtttg gttttcctga cacctcattt tataatccag atacacagcg ctggtttgg      300
gcctgtgtag gtgttgaggt aggccgtggt cagccattag gtgtgggcat tagtggccat     360
cctttattaa ataaattgga tgacacagaa atgctagtg cttatgcagc aaatgcaggt     420
gtggataata gagaatgtat atctatggat tacaaacaaa cacaattgtg tttaattggt     480
tgcaaaccac ctatagggga acactggggc aaaggatccc catgtaccaa tgttgcagta     540
aatccaggtg attgtccacc attagagtta ataaacacag ttattcagga tggtgatatg     600
gttgatactg ctttggtgc atgactttt actacattac aggctaacaa agtgaagtt       660
ccactggata tttgtacatc tatttgcaaa tatccagatt atattaaaat ggtgtcagaa     720
ccatatggcg acagcttatt ttttatttta cggagggaac aaatgttgt tagacatttta    780
tttaataggc tggtactgt tggtgaaaat gtaccgacg atttatacat taaaggctct     840
gggtctactg caaatttagc cagttcaaat tattttccta cacctagtgg ttctatggtt     900
acctctgatg cccaaatatt caataaacct tattggttac aacgagcaca gggccacaat     960
aatggcattt gttggggtaa ccaactattt gttactgttg ttgatactac acgcagtaca    1020
aatatgtcat tatgtgctgc catatctact tcagaaacta catataaaaa tactaacttt    1080
aaggagtacc tacgacatgg ggaggaatat gatttacagt ttatttttca actgtgcaaa    1140
ataaccttaa ctgcagacgt tatgacatac atacattcta tgaattccac tattttggag    1200
gactggaatt ttggtctaca acctccccca ggaggcacac tagaagatac ttataggttt    1260
gtaacatccc aggcaattgc ttgtcaaaaa ttagtggaag aaactagttt tattgatgct    1320
ggtgcaccat acactttttg ggaagtaaat ttaaaggaaa gttttctgc agacctagat    1380
cagtttcctt taggacgcaa attttttacta caagcaggat tgaaggccaa accaaaattt    1440
acattaggaa aacgaaaagc tacacccacc acctcatcta cctctacaac tgctaaacgc    1500
aaaaaacgta agctgtaa                                                   1518

<210> SEQ ID NO 9
```

<211> LENGTH: 505
<212> TYPE: PRT
<213> ORGANISM: Human papillomavirus

<400> SEQUENCE: 9

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400
```

```
Asp Trp Asn Phe Gly Leu Gln Pro Pro Gly Gly Thr Leu Glu Asp
            405                 410                 415

Thr Tyr Arg Phe Val Thr Ser Gln Ala Ile Ala Cys Gln Lys Leu Val
            420                 425                 430

Glu Glu Thr Ser Phe Ile Asp Ala Gly Ala Pro Tyr Thr Phe Trp Glu
            435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
            500                 505

<210> SEQ ID NO 10
<211> LENGTH: 1518
<212> TYPE: DNA
<213> ORGANISM: Human papillomavirus

<400> SEQUENCE: 10
atgtctcttt ggctgcctag tgaggccact gtctacttgc ctcctgtccc agtatctaag     60
gttgtaagca cggatgaata tgttgcacgc acaaacatat attatcatgc agggacatcc    120
agactacttg cagttggaca tccctatttt cctattaaaa aacctaacaa taacaaaata    180
ttagttccta agtatcagg attacaatac agggtattta gaatacattt acctgacccc     240
aataagtttg gttttcctga cacctcattt tataatccag atacacagcg gctggtttgg    300
gcctgtgtag gtgttgaggt aggccgtggt cagccattag gtgtgggcat tagtggccat    360
cctttattaa ataaattgga tgacacagaa aatgctagtg cttatgcagc aaatgcaggt    420
gtggataata gagaatgtat atctatggat tacaaacaaa cacaattgtg tttaattggt    480
tgcaaaccac ctataggga acactggggc aaaggatccc catgtaccaa tgttgcagta    540
aatccaggtg attgtccacc attagagtta ataaacacag ttattcagga tggtgatatg    600
gttgatactg gctttggtgc tatggacttt actacattac aggctaacaa agtgaagtt     660 ccactggata tttgtacatc tatttgcaaa tatccagatt atattaaaat ggtgtcagaa    720
ccatatggcg acagcttatt tttttattta cggagggaac aaatgtttgt tagacattta    780
tttaataggg ctggtactgt tggtgaaaat gtaccgacg atttatacat taaaggctct    840
gggtctactg caaatttagc cagttcaaat tattttccta cacctagtgg ttctatggtt    900
acctctgatg cccaaatatt caataaacct tattggttac aacgagcaca gggccacaat    960
aatggcattt gttggggtaa ccaactattt gttactgttg ttgatactac acgcagtaca   1020
aatatgtcat tatgtgctgc catatctact tcagaaacta catataaaaa tactaacttt   1080
aaggagtacc tacgacatgg ggaggaatat gatttacagt ttatttttca actgtgcaaa   1140
ataaccttaa ctgcagacgt tatgacatac atacattcta tgaattccac tattttggag   1200
gactggaatt ttggtctaca acctccccca ggaggcacat tagtggaaga aactagtttt   1260
attgatgctg gtgcaccagc ttgtcaaaaa catacacctc agcacctaa agaagatccc   1320 cttaaaaaat acactttttg ggaagtaaat ttaaaggaaa gttttctgc agacctagat   1380 cagtttcctt taggacgcaa attttactac caagcaggat tgaaggccaa accaaaattt   1440
acattaggaa aacgaaaagc tacacccacc acctcatcta cctctacaac tgctaaacgc   1500
```
aaaaaacgta agctgtaa                                                                1518

<210> SEQ ID NO 11
<211> LENGTH: 505
<212> TYPE: PRT
<213> ORGANISM: Human papillomavirus

<400> SEQUENCE: 11

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr

```
                370             375             380
Ala Asp Val Met Thr Tyr Ile His Ser Met Asn Ser Thr Ile Leu Glu
385                     390                 395                 400

Asp Trp Asn Phe Gly Leu Gln Pro Pro Gly Thr Leu Val Glu
                405                 410                 415

Glu Thr Ser Phe Ile Asp Ala Gly Ala Pro Ala Cys Gln Lys His Thr
                420                 425                 430

Pro Pro Ala Pro Lys Glu Asp Pro Leu Lys Lys Tyr Thr Phe Trp Glu
                435                 440                 445

Val Asn Leu Lys Glu Lys Phe Ser Ala Asp Leu Asp Gln Phe Pro Leu
        450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                    485                 490                 495

Thr Ala Lys Arg Lys Lys Arg Lys Leu
                500                 505

<210> SEQ ID NO 12
<211> LENGTH: 1518
<212> TYPE: DNA
<213> ORGANISM: Human papillomavirus

<400> SEQUENCE: 12
atgtctcttt ggctgcctag tgaggccact gtctacttgc ctcctgtccc agtatctaag      60
gttgtaagca cggatgaata tgttgcacgc acaaacatat attatcatgc agggacatcc     120
agactacttg cagttggaca tccctatttt cctattaaaa aacctaacaa taacaaaata     180
ttagttccta agtatcagg attacaatac agggtattta gaatacattt acctgacccc      240
ttagtggaag aaactagttt tattgatgct ggtgcaccag atacacagcg gctggtttgg     300
gcctgtgtag gtgttgaggt aggccgtggt cagccattag gtgtgggcat tagtggccat     360
cctttattaa ataaattgga tgacacagaa aatgctagtg cttatgcagc aaatgcaggt     420
gtggataata gagaatgtat atctatggat acaaaacaaa cacaattgtg tttaattggt     480
tgcaaaccac ctatagggga acactggggc aaaggatccc catgtaccaa tgttgcagta     540
aatccaggtg attgtccacc attagagtta ataaacacag ttattcagga tggtgatatg     600
gttgatactg gctttggtgc tatggacttt actacattac aggctaacaa agtgaagtt      660 ccactggata tttgtacatc tatttgcaaa tatccagatt atattaaaat ggtgtcagaa     720
ccatatggcg acagcttatt tttttattta cggagggaac aaatgtttgt tagacattta     780
tttaataggg ctggtactgt tggtgaaaat gtaccgacg atttatacat taaaggctct     840
gggtctactg caaatttagc cagttcaaat tattttccta cacctagtgg ttctatggtt     900
acctctgatg cccaaatatt caataaacct tattggttac aacgagcaca gggccacaat     960
aatggcattt gttggggtaa ccaactattt gttactgttg ttgatactac acgcagtaca    1020
aatatgtcat tatgtgctgc catatctact tcagaaacta catataaaaa tactaacttt    1080
aaggagtacc tacgacatgg ggaggaatat gatttacagt ttatttttca actgtgcaaa    1140
ataaccttaa ctgcagacgt tatgacatac atacattcta tgaattccac tattttggag    1200
gactggaatt ttggtctaca acctccccca ggaggcacac tagaagatac ttataggttt    1260
gtaacatccc aggcaattgc ttgtcaaaaa catacacctc cagcacctaa gaagatccc     1320 cttaaaaaat acactttttg ggaagtaaat ttaaaggaaa agttttctgc agacctagat    1380
```

```
cagtttcctt taggacgcaa atttttacta caagcaggat tgaaggccaa accaaaattt    1440
acattaggaa aacgaaaagc tacacccacc acctcatcta cctctacaac tgctaaacgc    1500
aaaaaacgta agctgtaa                                                  1518
```

<210> SEQ ID NO 13
<211> LENGTH: 505
<212> TYPE: PRT
<213> ORGANISM: Human papillomavirus

<400> SEQUENCE: 13

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Leu Val Glu Glu Thr Ser Phe Ile Asp Ala Gly Ala Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350
```

-continued

```
Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 14
<211> LENGTH: 39
<212> TYPE: DNA
<213> ORGANISM: Human papillomavirus

<400> SEQUENCE: 14
ttagtggaag aaactagttt tattgatgct ggtgcacca                            39
```